United States Patent
Patel

(10) Patent No.: US 12,362,059 B2
(45) Date of Patent: Jul. 15, 2025

(54) NEUROSTIMULATION WITH GAMIFIED SELF-CONTROL TRAINING EXERCISES

(71) Applicant: NXTech Inc, Attleboro, MA (US)

(72) Inventor: Salil H. Patel, Houston, TX (US)

(73) Assignee: NXTech Inc, Attleboro, MA (US)

( * ) Notice: Subject to any disclaimer, the term of this patent is extended or adjusted under 35 U.S.C. 154(b) by 0 days.

(21) Appl. No.: 18/601,371

(22) Filed: Mar. 11, 2024

(65) Prior Publication Data

US 2024/0212827 A1 Jun. 27, 2024

Related U.S. Application Data

(63) Continuation-in-part of application No. 18/360,111, filed on Jul. 27, 2023.

(60) Provisional application No. 63/527,241, filed on Jul. 17, 2023.

(51) Int. Cl.
| | |
|---|---|
| *A61N 1/20* | (2006.01) |
| *A61N 1/36* | (2006.01) |
| *A61N 5/06* | (2006.01) |
| *A63F 13/21* | (2014.01) |
| *A63F 13/212* | (2014.01) |
| *G16H 20/70* | (2018.01) |

(52) U.S. Cl.
CPC ............... *G16H 20/70* (2018.01); *A61N 1/20* (2013.01); *A63F 13/21* (2014.09); *A63F 13/212* (2014.09); *A61N 5/0613* (2013.01)

(58) Field of Classification Search
CPC .......... G16H 20/70; G16H 20/30; A61N 1/20; A61N 5/0613; A61N 1/0456; A61N 2/006; A63F 13/21; A63F 13/212
See application file for complete search history.

(56) References Cited

U.S. PATENT DOCUMENTS

| | | | |
|---|---|---|---|
| 8,494,627 | B2 | 7/2013 | Bikson et al. |
| 9,339,642 | B1 | 5/2016 | Bikson et al. |
| 9,630,005 | B2 | 4/2017 | Wingeier et al. |
| 9,757,561 | B2 | 9/2017 | Wingeier et al. |
| 9,802,042 | B2 | 10/2017 | Wingeier et al. |
| 10,143,842 | B2 | 12/2018 | Wingeier et al. |
| 10,484,502 | B1 | 11/2019 | Klein et al. |
| 10,898,711 | B1 | 1/2021 | Phillips et al. |
| 11,097,097 | B2 | 8/2021 | Wingeier et al. |
| 11,122,998 | B2 | 9/2021 | Martucci et al. |

(Continued)

FOREIGN PATENT DOCUMENTS

| | | |
|---|---|---|
| WO | 2019161050 A1 | 8/2019 |
| WO | 2022086454 A1 | 4/2022 |

OTHER PUBLICATIONS

International Search Report and Written Opinion regarding corresponding PCT Pub. No. PCT/US2024/038048; issued Oct. 30, 2025.

*Primary Examiner* — Paula J Stice

(74) *Attorney, Agent, or Firm* — DICKINSON WRIGHT PLLC

(57) ABSTRACT

Systems and methods for managing self-control impairment. The method includes placing a neurostimulation device on a head of a user. The method also includes displaying, to the user via a graphical user interface of a mobile computing device, a self-control training boost game. The method further includes activating the neurostimulation device to provide a transcranial stimulation to the user while the user plays the self-control training boost game.

20 Claims, 23 Drawing Sheets

(56) References Cited

U.S. PATENT DOCUMENTS

| | | |
|---|---|---|
| 11,464,972 B2 | 10/2022 | Wingeier et al. |
| 2011/0144716 A1 | 6/2011 | Bikson et al. |
| 2012/0203346 A1 | 8/2012 | Bikson et al. |
| 2017/0148343 A1 | 5/2017 | Merzenich et al. |
| 2017/0368297 A1* | 12/2017 | Tyler .................. A61N 1/36034 |
| 2018/0256888 A1* | 9/2018 | Wingeier ............. A61N 1/0492 |
| 2019/0151654 A1* | 5/2019 | Wingeier ............. A61N 1/3603 |
| 2019/0343447 A1 | 11/2019 | Mateus et al. |
| 2020/0060603 A1 | 2/2020 | Bower et al. |
| 2020/0114116 A1 | 4/2020 | Alailima |
| 2020/0187777 A1 | 6/2020 | Luderer et al. |
| 2020/0372990 A1 | 11/2020 | Ho |
| 2020/0380882 A1 | 12/2020 | Alailima et al. |
| 2021/0050090 A1 | 2/2021 | Klein et al. |
| 2021/0226930 A1 | 7/2021 | McFarland et al. |
| 2022/0005581 A1 | 1/2022 | Brown et al. |
| 2022/0039714 A1 | 2/2022 | Johnson et al. |

\* cited by examiner

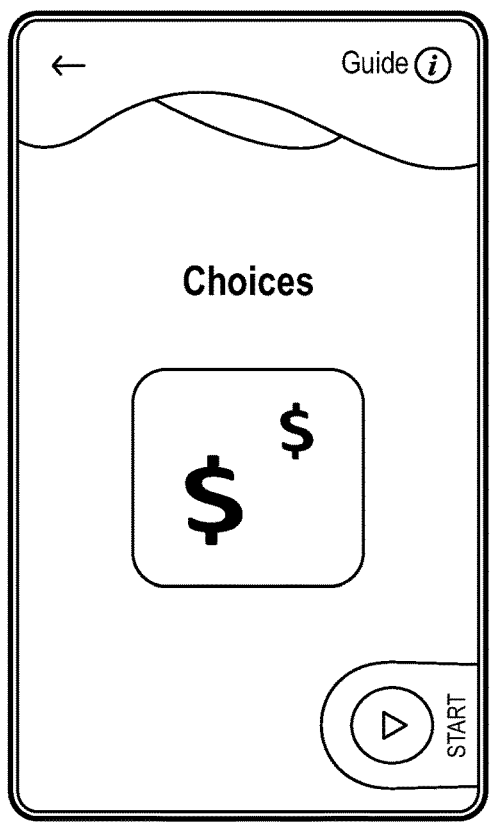
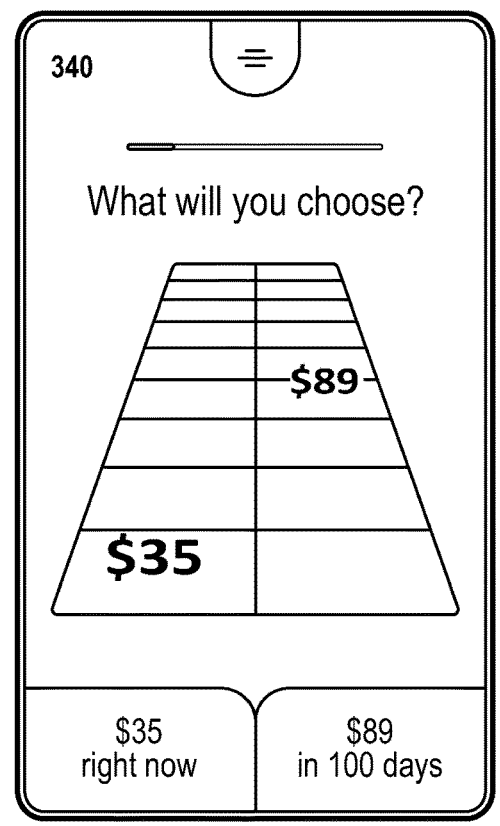
FIG. 14A
FIG. 14B
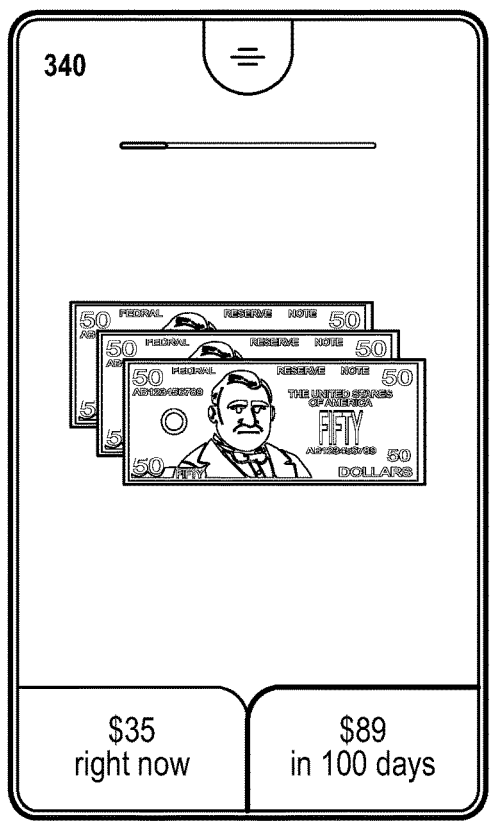
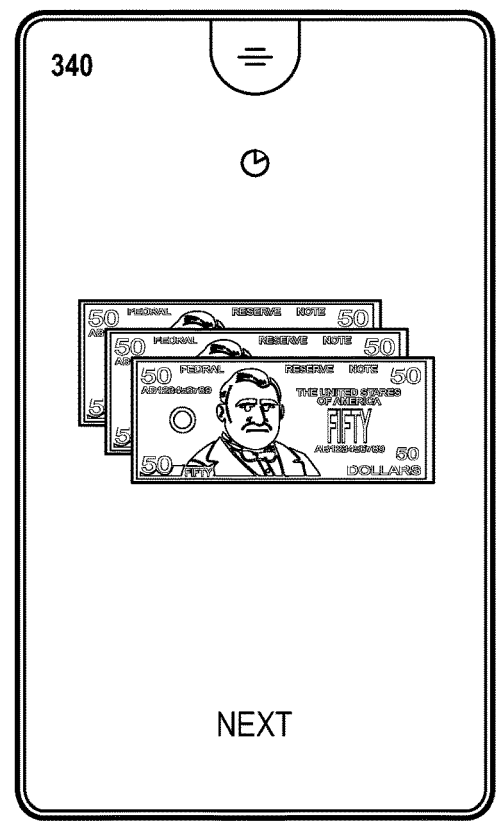
FIG. 14C
FIG. 14D

NEUROSTIMULATION WITH GAMIFIED SELF-CONTROL TRAINING EXERCISES

CROSS-REFERENCE TO RELATED APPLICATIONS

This application is a continuation-in-part of and claims priority to and the benefit of U.S. utility patent application Ser. No. 18/360,111, filed Jul. 27, 2023, titled "SUBSTANCE USAGE MANAGEMENT WITH GAMIFIED SELF-CONTROL TRAINING EXERCISES," which claims priority to and the benefit of U.S. Provisional Application Ser. No. 63/527,241, filed Jul. 17, 2023, titled "SUBSTANCE USAGE MANAGEMENT WITH GAMIFIED SELF-CONTROL TRAINING EXERCISES," the entire disclosures of which are hereby incorporated by reference for all purposes.

BACKGROUND

Inappropriate drug use has been the direct cause of over 900,000 deaths in the United States since 1999, with an estimated 74% of overdoses involving opioids. The magnitude of harm attributable to substance dependency and addiction presents a substantial ongoing health burden. The rising tide of mortality and morbidity due to opioid misuse, in particular, prompted the Centers for Disease Control and Prevention to declare the opioid crisis a public health emergency. Nearly two million Americans suffer from Opioid Use Disorder (OUD) as a chronic medical condition. One to three million additional individuals suffer from complex persistent opioid dependence as a consequence of long term use of prescribed opioids for pain control. Opioid addiction and opioid dependency may co-occur with dependencies upon other substances, for example, alcohol and sedatives, which often share common factors driving use, re-use, and relapse during recovery. Some treatments for problematic substance use include pharmacotherapy and psychotherapy, which may be intended to promote attempted abstinence, or to encourage a reduction in substance ingestion. However, these treatment strategies exhibit substantial limitations in efficacy, due to, for example, poor real-world accessibility or an ongoing desire to use drugs. Drop-off from clinically managed treatment programs for OUD is between 37% and 60% over the first year of maintenance. Further, overall relapse rates even with intensive treatments are between 40% and 60% by six months, and 72% to 88% by thirty-six months. Associated economic costs to society from unmanaged substance use are estimated to be about 500 billion dollars annually.

Neurotrauma including anoxic brain injury and traumatic brain injury (TBI) affects millions of individuals world wide. TBI, specifically, is a condition that affects about 2.4 million individuals, leading to about 190 daily deaths in the United States. TBI represents a major cause of functional impairment and disability worldwide. Beyond a range of physical impairments associated with moderate-to-severe TBI, psychiatric conditions (for example, post-traumatic stress disorder (PTSD) and major depressive disorder (MDD)) are known to arise in the setting of mild TBI, and subclinical neurotrauma more generally. The overall increase in mortality observed in populations aged 55 and above living with chronic neurotrauma is likely due to this constellation of multiple end-effects.

Impulsivity is a major psychological sequelae of neurotrauma including TBI. A rise in impulsivity emerging after a TBI, in particular, is designated as a pathological "personality change" under the DSM-V criteria. In clinical practice, impulsivity in TBI is often unaddressed or undertreated by existing occupational, physical, and behavioral therapy strategies, particularly in the context of outpatient rehabilitation and at-home recovery. No FDA-approved or cleared treatment for self-control impairment in TBI exists. In addition, no tools exist to allow for continuous (for example, weekly) measurement of self-control as an aspect of TBI diagnosis or treatment monitoring.

SUMMARY

Self-control training is a behavioral model which may be applied to improve patient-directed recovery from substance use disorders, substance dependencies, neurotrauma, stroke, and trauma-related disorders. Self-control training exercises may include, but are not limited to, experiential, procedural, and choice-making activities, and may be provided to a user in the form of games played on a smartphone, desktop computer, or other computing device. Self-control training exercises may include, for example, cognitive activities designed to activate, engage, or modulate processes including, for example, working memory, selective attention, procedural memory, inhibitory control, ecological assessment, and other neurological circuits implicated in cognitive flexibility. Given the abundant usage of smartphones, gamified self-control training exercises can be provided to nearly any user at any time. For example, gamified self-control training exercises can be provided to a user on their smartphone as a just in time intervention during a substance craving. Further, neurostimulation (for example, anodal or cathodal transcranial direct current stimulation (tDCS)) is a treatment that may be applied to improve patient-directed recovery from neurotrauma such as anoxic or traumatic brain injury. The present disclosure provides, among other things, self-control impairment management with gamified cognitive activities in combination with neurostimulation. The gamified cognitive activities include self-control training exercises configured to increase, among other things, a user's impulse control capability.

The present disclosure provides a method for managing self-control impairment. The method includes placing a neurostimulation device on a head of a user. The method also includes displaying, to the user via a graphical user interface of a mobile computing device, a self-control training (SCT) boost game. The method further includes activating the neurostimulation device to provide a transcranial stimulation to the user while the user plays the SCT boost game.

The present disclosure also provides a system for managing self-control impairment. The system includes, in one implementation, a neurostimulation device, a graphical user interface, one or more memory devices, and one or more processing devices. The neurostimulation device is configured to be worn on a head of a user. The one or more memory devices are for storing instructions. The one or more processing devices are configured to execute the instructions to display, to the user via the graphical user interface, a self-control training (SCT) boost game. The one or more processing devices are also configured to execute the instructions to activate the neurostimulation device to provide a transcranial stimulation to the user while the user plays the SCT boost game.

Other technical features may be readily apparent to one skilled in the art from the following figures, descriptions, and claims.

BRIEF DESCRIPTION OF THE DRAWINGS

For a more complete understanding of the present disclosure and its advantages, reference is now made to the following description, taken in conjunction with the accompanying drawings. It is emphasized that, according to common practice, the various features of the drawings are not necessarily to-scale. On the contrary, the dimensions of the various features may be—and typically are—arbitrarily expanded or reduced for the purpose of clarity.

FIGS. 14A through 14D are screen shots of an example of a choices game used in a check-in session, in accordance with some implementations of the present disclosure.

NOTATION AND NOMENCLATURE

Figure 1A:
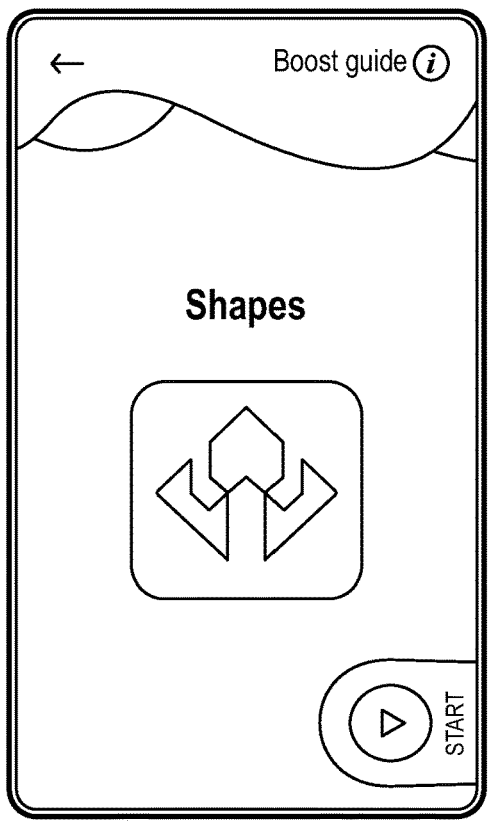
FIGS. 1A through 1D are screen shots of an example of a shapes game that provides a low cognitive load, in accordance with some implementations of the present disclosure.
Figure 1B:
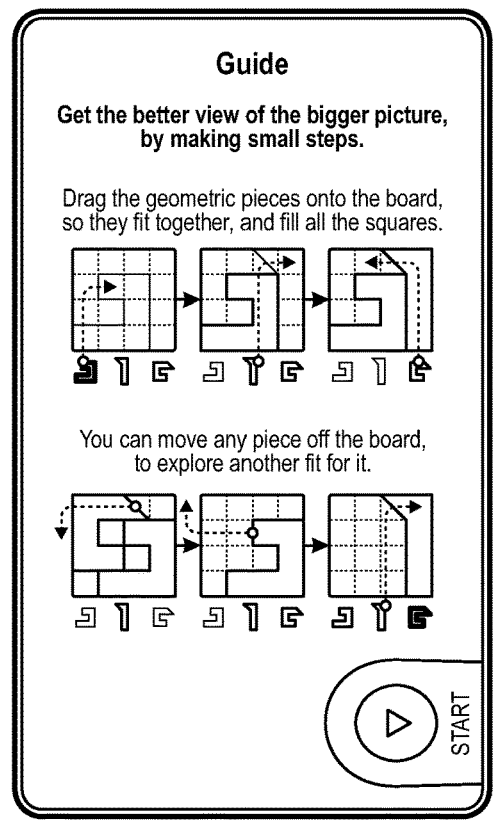
Figure 1C:
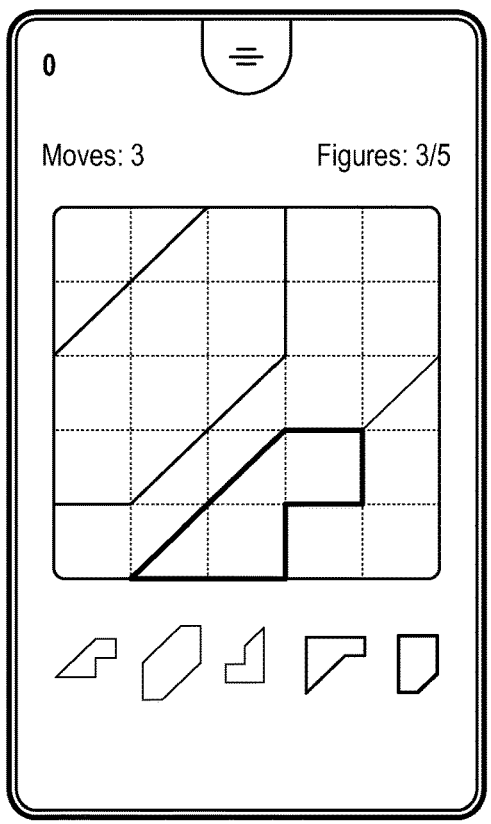
Figure 1D:
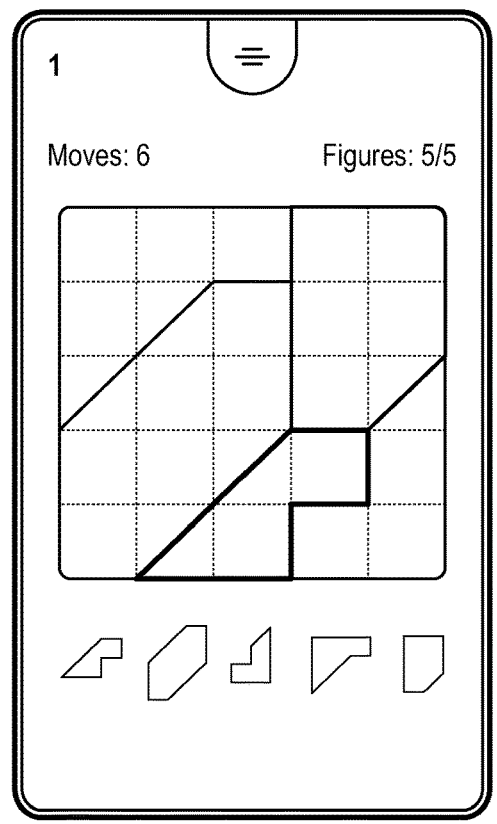
Figure 2A:
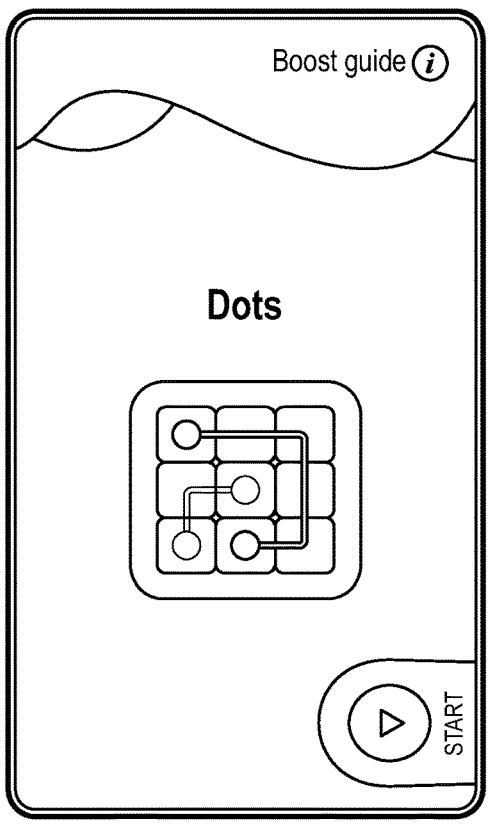
FIGS. 2A through 2D are screen shots of an example of a dots game that provides a low cognitive load, in accordance with some implementations of the present disclosure.
Figure 2B:
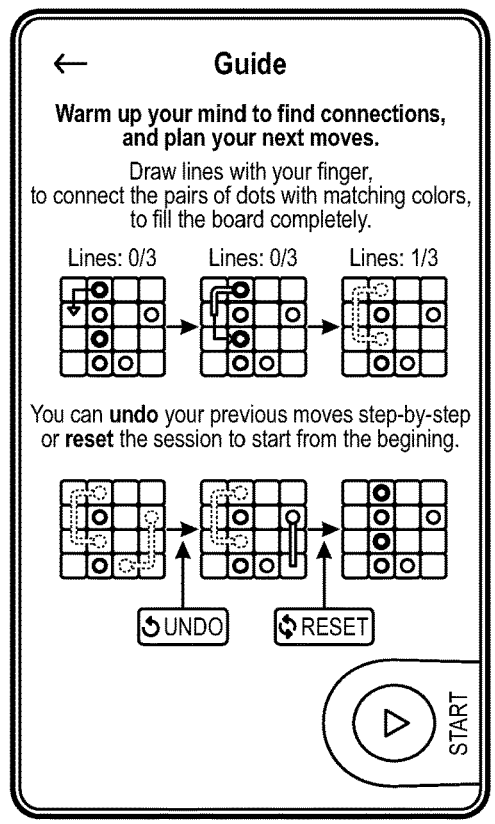
Figure 2C:
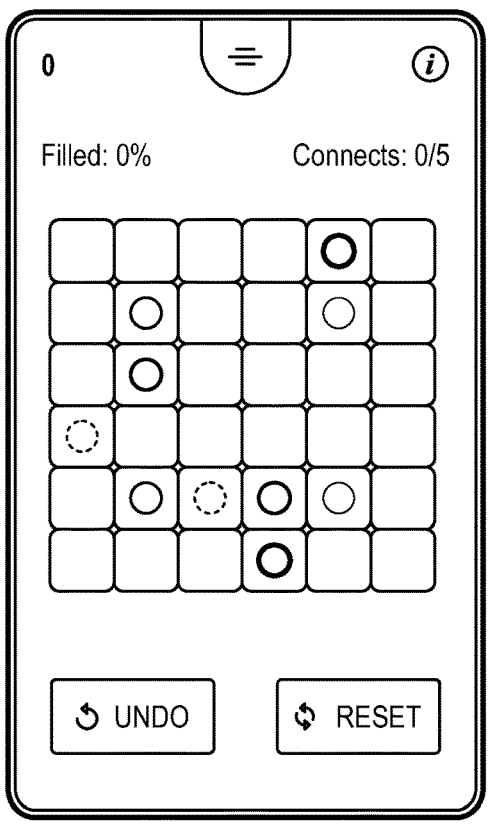
Figure 2D:
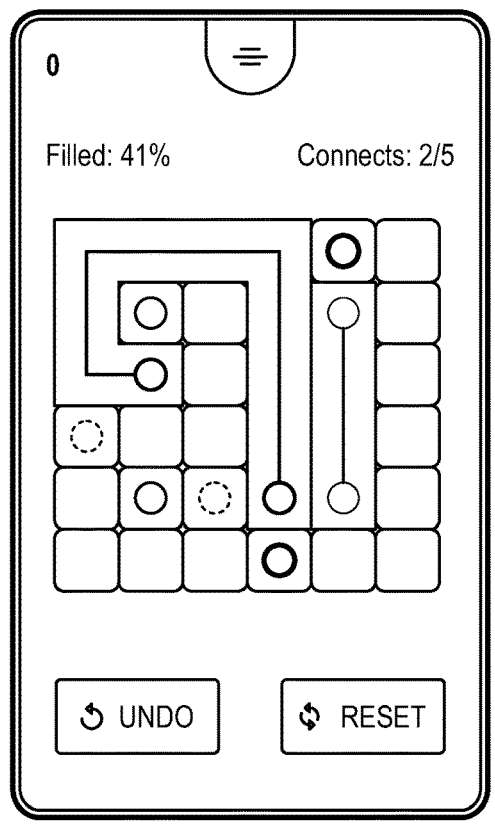

Various terms are used to refer to particular system components. A particular component may be referred to commercially or otherwise by different names. Further, a particular component (or the same or similar component) may be referred to commercially or otherwise by different names. Consistent with this, nothing in the present disclosure shall be deemed to distinguish between components that differ only in name but not in function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection, or through an indirect connection via other devices and connections.

The terminology used herein is for the purpose of describing particular example implementations only, and is not intended to be limiting. As used herein, the singular forms "a," "an," "the," and "said" may be intended to include the plural forms as well, unless the context clearly indicates otherwise. The terms "a," "an," "the," and "said" as used herein in connection with any type of processing component configured to perform various functions may refer to one processing component configured to perform each and every function, or a plurality of processing components collectively configured to perform each of the various functions. By way of example, "A processor" configured to perform actions A, B, and C may refer to one processor configured to perform actions A, B, and C. In addition, "A processor" configured to perform actions A, B, and C may also refer to a first processor configured to perform actions A and B, and a second processor configured to perform action C. Further, "A processor" configured to perform actions A, B, and C may also refer to a first processor configured to perform action A, a second processor configured to perform action B, and a third processor configured to perform action C. The method steps, processes, and operations described herein are not to be construed as necessarily requiring their performance in the particular order discussed or illustrated, unless specifically identified as an order of performance. It is also to be understood that additional or alternative steps may be employed.

The terms first, second, third, etc. may be used herein to describe various elements, components, regions, layers and/or sections; however, these elements, components, regions, layers and/or sections should not be limited by these terms. These terms may be only used to distinguish one element, component, region, layer, or section from another region, layer, or section. Terms such as "first," "second," and other numerical terms, when used herein, do not imply a sequence or order unless clearly indicated by the context. Thus, a first element, component, region, layer, or section discussed below could be termed a second element, component, region, layer, or section without departing from the teachings of the example implementations. The phrase "at least one of," when used with a list of items, means that different combinations of one or more of the listed items may be used, and only one item in the list may be needed. For example, "at least one of: A, B, and C" includes any of the following combinations: (i) A, B, and C; (ii) A and B; (iii) A and C; (iv) B and C; (v) A; (vi) B; and (vii) C. In another example, the phrase "one or more" when used with a list of items means there may be one item or any suitable number of items exceeding one.

Spatially relative terms, such as "inner," "outer," "beneath," "below," "lower," "above," "up," "upper," "top," "bottom," "down," "inside," "outside," "contained within," "superimposing upon," and the like, may be used herein. These spatially relative terms can be used for ease of description to describe one element's or feature's relationship to another element(s) or feature(s) as illustrated in the figures. The spatially relative terms may also be intended to encompass different orientations of the device in use, or operation, in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptions used herein interpreted accordingly.

A "healthcare professional" may refer to a doctor, physician assistant, nurse, nurse practitioner, chiropractor, dentist, physical therapist, and the like. A "healthcare professional" may also refer to any person with a credential, license, or degree in the field of medicine, physical therapy, or rehabilitation. A "healthcare professional" may also refer to any person who has received training in health and wellness support but has not necessarily obtained a related certification or license, such as a peer recovery coach, rehabilitation sponsor, and the like. As used herein, and without limiting the foregoing, a "healthcare professional" may be a human being, a robot, a virtual assistant, a virtual assistant in virtual and/or augmented reality, or an artificially intelligent entity, such entity including a software program, integrated software and hardware, or hardware alone.

DETAILED DESCRIPTION

The following discussion is directed to various implementations of the present disclosure. Although one or more of these implementations may be preferred, the implementations disclosed should not be interpreted, or otherwise used, as limiting the scope of the present disclosure, including the claims. In addition, one skilled in the art will understand that the following description has broad application, and the discussion of any implementation is meant only to be exemplary of that implementation, and not intended to intimate that the scope of the present disclosure, including the claims, is limited to that implementation.

From a behavioral science perceptive, a substance craving may be described as a momentary self-control depletion event that is modulated by cognitive circuits operating in the seconds-to-minutes time range. Relapse prevention techniques include practices for addressing substance cravings, and in particular drug cravings, by orienting a person's focus toward the triggers of their drug use. Relapse prevention techniques also include activities intended to support coping in the moment of a craving. Current cue-oriented relapse prevention techniques for substance use disorders show effect in controlled and intensive-intervention settings, but exhibit high drop-off in outpatient treatment situations. For example, the high logistic burden that current structured relapse prevention techniques impose leads to high levels of drop-off. Further, the cognitive resources required to complete current relapse prevention techniques (for example, higher-order introspection and planning functions) are often so significant that real-world effectiveness is poor.

Broadly, individuals with uncontrolled cravings or ongoing withdrawal symptoms and impaired impulse control exhibit poorer treatment outcomes during treatment for substance dependency. Pharmacotherapy-based treatment, also known as substitution therapy or medication assisted therapy, for substance use disorders (for example, methadone, suboxone, or buprenorphine for opioid addiction, and disulfuram for alcohol addiction) are among the most evidence-based methods for behavior change in these conditions. Pharmacotherapy for opioid use disorder specifically is typically offered to treat illicit opioid abuse, and is intended to alleviate withdrawal signs and other manifest signs of chronic physiologic cravings (e.g., physiologic, background urges). However, acute cravings (i.e., sharp, often cue-induced urges) are persistent and pervasive phenomena in pharmacotherapy and other treatments, resulting in increased risk for substance re-use and relapse. Therefore, cravings burden and momentary self-control are related targets for harm-reduction in substance abuse and dependency recovery. However, limited patient-directed, on-demand options are available to individuals for these issues, even as part of supervised treatment programs.

In addition to the foregoing, a substantial population is chronically-dependent upon prescribed opioids. While these individuals may not meet diagnostic criteria for opioid use disorder, these individuals may be candidates for harm-reduction strategies which improve self-control. Such individuals may follow a pharmacotherapy regimen known as Long Term Opioid Therapy (LTOT), usually to treat chronic non-cancer pain. LTOT is recognized to confer higher potential for overdose death, as well as for morbidities including gastrointestinal and genitourinary dysfunction, sleep disorders, mood disorders, and other impairments. Despite strong recommendations from public health agencies and medical organizations that individuals should migrate away from LTOT, limited options exist to support individuals in reducing and managing opioid usage at scheduled dose intervals. Many individuals attempting LTOT are reported to return to substance usage within weeks or months. The behavioral drivers of drop-off and failure in LTOT are similar to those in medication assisted therapy, relating primarily to momentary challenges to self-control. Additional drivers may include breakthrough pain symptoms and sleep/wake dysfunction. These drivers may preclude effective substance usage management.

Momentary self-control (i.e., choice preference in the seconds to minutes range) is an important factor in harm-reduction for opioid addiction and opioid dependency treatment. Impulsivity traits are a primary endophenotype for substance use disorders including opioid use disorder. For example, choices involving trade-offs between amount and delay are considered impulsive whenever a smaller-sooner reward is sub-optimally preferred over a longer-later reward that is either hypothetical or real. Thus, impulsive choice may be characterized as an unwillingness to wait to obtain a larger reward. Generally, individuals with higher self-control display a range of better quality of life outcomes than individuals with lower self-control. Impulsivity may form a central locus (influenced by, for example, neurobiological, genetic, and environmental factors) that increases the risks of disease development and progression. Higher levels of impulsive choice may in fact be associated with the development of substance use disorders from the outset. Impulsive choice-making can predict poor treatment outcomes as short-horizon outcomes (for example, drug usage) can overwhelm commitment to long-term goals, creating barriers to treatment self-efficacy and retention. Self-control training is a behavioral model that may be applied for craving support in substance use disorders and to address impulsive choice making.

Self-control training may be implemented in an electronic user interaction system involving exercises (for example, challenges or tasks) which activate, engage, or modulate processes including memory and attention or other neural circuits implicated in bottom-up or top-down operations such as visuospatial processing, motor control, sensation, planning, executive inhibition, reward-seeking behavior, and goal-directed behavior. A self-control training exercise may activate a perceptually-linked process (for example, a memory process, an attention process, an ecological assessment process, or a cognitive flexibility process). Alternatively, or in addition, a self-control training exercise may activate a choice-making process relating to, for example, the accumulation or disposition of rewards (whether hypothetical or real). Perceptually-linked tasks and choice-making tasks may be presented in isolation or in combination as part of a larger training session. A subset of self-control training exercises may recruit and reinforce cognitive perceptual processes relating to time such as tasks involving time perception, timing accuracy, and delay tolerance.

The delay of gratification paradigm and the shifting focus framework are examples of strategies for cognitive self-control training which can be implemented for long-term alteration of suppressed control and motivational circuits in substance use disorders with a significant potential for higher-order, self-efficacy benefits. Self-control training exercises and sessions may incorporate frameworks and paradigms which are projective, retrospective, or experiential in nature, and may comprise both continuous and asynchronous components. Cognitive load is a factor which may modulate acceptability and efficacy of training exercises. Cognitive loading reflects the instantaneous propensity to receive and store information, including the capacity for such information to result in task-specific learning and generic-cognitive encoding. In this construct, the physiologic and psychologic state of the individual may affect cognitive loading, and the presence of stressors (for example, cravings) may reduce available cognitive capacity in the working memory domain. In addition, in reciprocal fashion, relative cognitive load may be manifest in physiologic signs. Depending on the chosen framework, exercises may incorporate visual, auditory, or tactical (for example, haptic) components for task presentation and user interaction, and for which cue-induced or prompt-related user responses may indicate relative cognitive loading.

Psychometrically-measurable executive dysfunctions abate during sustained substance dependency recovery due to, for example, increased attention towards the future and improved working memory processing. Some processes for moderating impulsive decision-making include working memory, timing ability, inhibitory control, and delay tolerance. For example, short-term memory training is linked to generalized improvements in working memory capabilities.

In general, a successful intervention for substance dependency should be long-lasting and show a significant maintenance of the effects over time. Studies in rodents have reported that the effects of self-control training intervention were seen for at least nine months without significant deterioration of effects. Further, self-control training interventions have shown positive test-retest reliability over periods of up to one year, which indicates that impulsive choice is a relatively-stable trait. The effects of self-control training interventions indicate that impulsive choices, and related cognitive processes, are malleable despite being stable. Self-control training interventions increase longer-later choices in typically-developing healthy adults as well as adults and children with mental health disorders such as attention-deficit/hyperactivity disorder.

The present disclosure provides systems and methods for substance usage management with a plurality of gamified self-control training exercises (referred to herein as "boost games"). Each boost game includes a form of repeating trials, sequences, or turns, as will be described in more detail below. Collectively, the plurality of boost games are configured to shift a user's selective attention away from their internal qualia and deliver brief sessions of self-control training (for example, between one minute and ten minutes). Individually, each of the plurality boost games is configured to provide a low, moderate, or high cognitive load to the user, as will be described in more detail below. In some implementations, user completion of boost games, relative to task performance, leads to the accumulation of rewards (for example, points) which are tracked by the system. In some boost games, rewards may be subject to probabilistic or delay-related accumulation or disposition choices for which user responses are recorded and collected by the system, and may additionally be used for calibration and user-state profiling.

One or more of the boost games are configured to provide low cognitive loads to avoid overloading a user. Boost games configured to provide low cognitive loads are sometimes referred to herein as "stage one boost games." Stage one boost games are configured to target the cognitive processes of selective attention, physical motion, awareness, or a combination thereof. For example, FIGS. 1A through 1D are screen shots of a shapes game that provides a low cognitive load and targets the cognitive process of selective attention. The shapes game includes a tiling puzzle. In some implementations, the shapes game is a variation of the game Tangram. For example, the objective of the shapes game may be to find a correct placement for a set of polygons on a square gridded board. As a further example of a stage one boost game, FIGS. 2A through 2D are screen shots of a dots game that provides a low cognitive load and targets the cognitive process of selective attention. The dots game may include a spatial puzzle. For example, gameplay in the dots game may represent the connection of multiple pairs of points on a closed board, without intersections.

To target the cognitive process of physical motion, a stage one boost game may include, for example, a game in which human faces with different expressions are displayed to a user and the user is instructed to replicate the displayed facial expressions. For example, a happy face may be displayed on a display of a smartphone and a camera of the smartphone is used determine whether the user is replicating the happy face. Further, to target the cognitive process of awareness, a stage one boost game may include, for example, a game in which a user is prompted to find and take a picture of an object with a specific attribute that is located in the room. For example, a user may be prompted to find and take a picture of an object in the room that is blue.

Figure 3A:
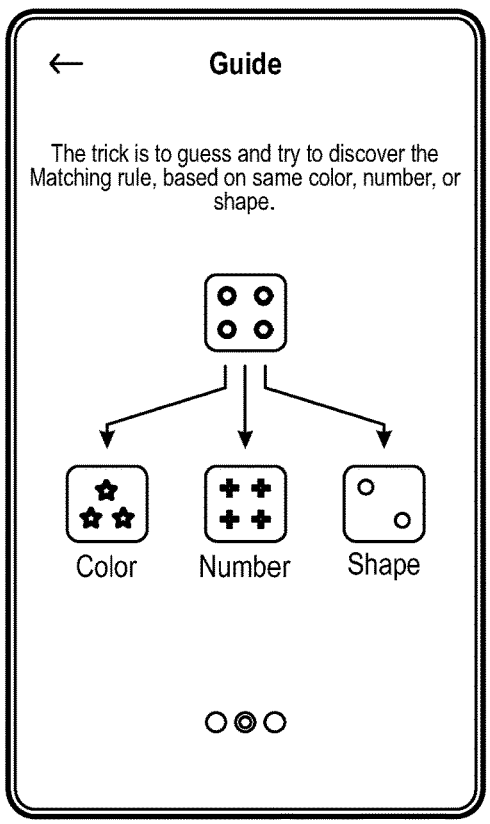
FIGS. 3A through 3D are screen shots of an example of a match game that provides a moderate cognitive load, in accordance with some implementations of the present disclosure.
Figure 3B:
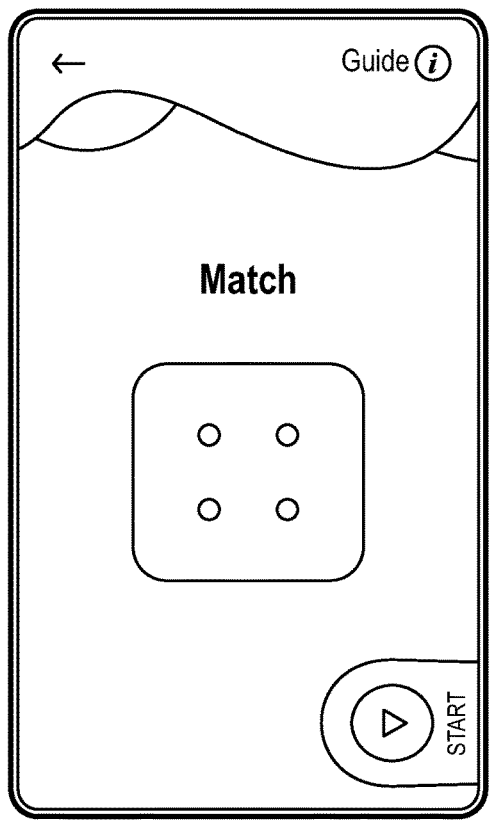
Figure 3C:
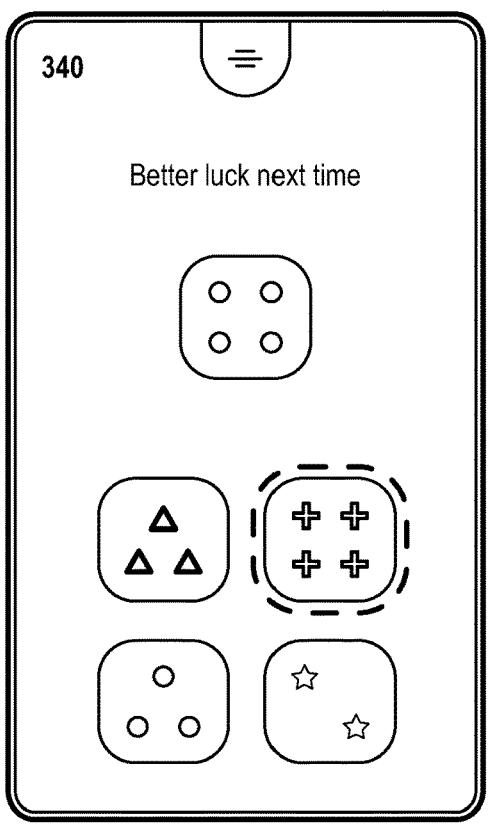
Figure 3D:
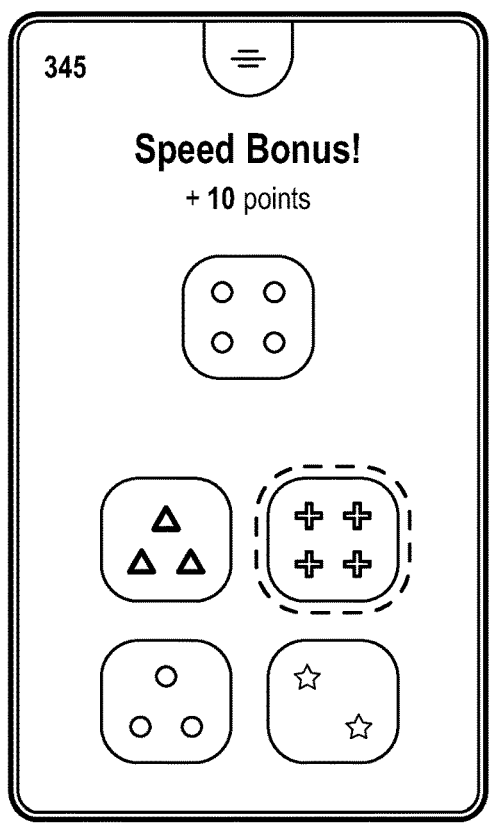
Figure 4A:
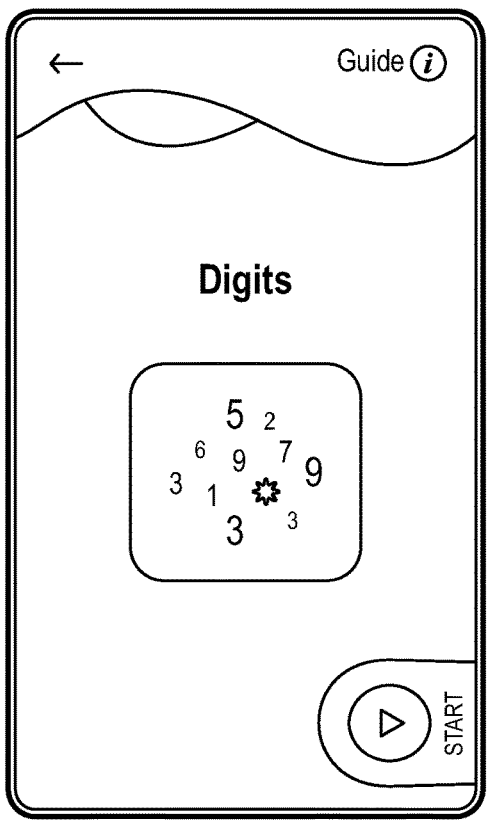
FIGS. 4A through 4D are screen shots of an example of a digits game that provides a moderate cognitive load, in accordance with some implementations of the present disclosure.
Figure 4B:
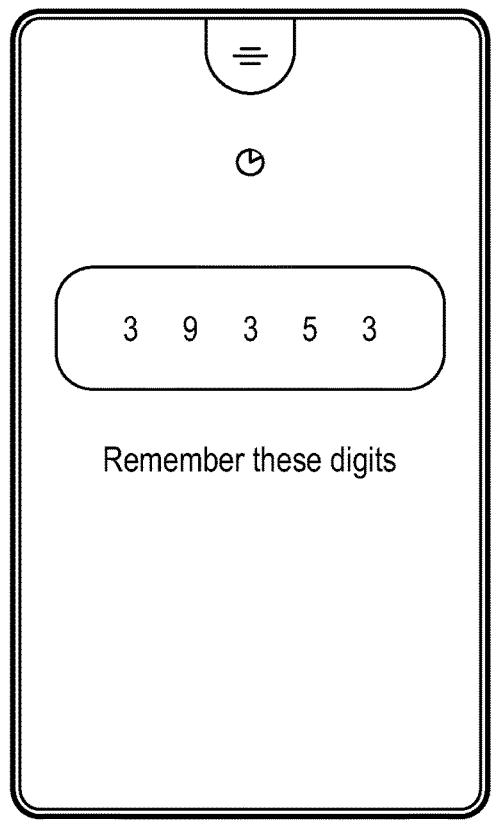
Figure 4C:
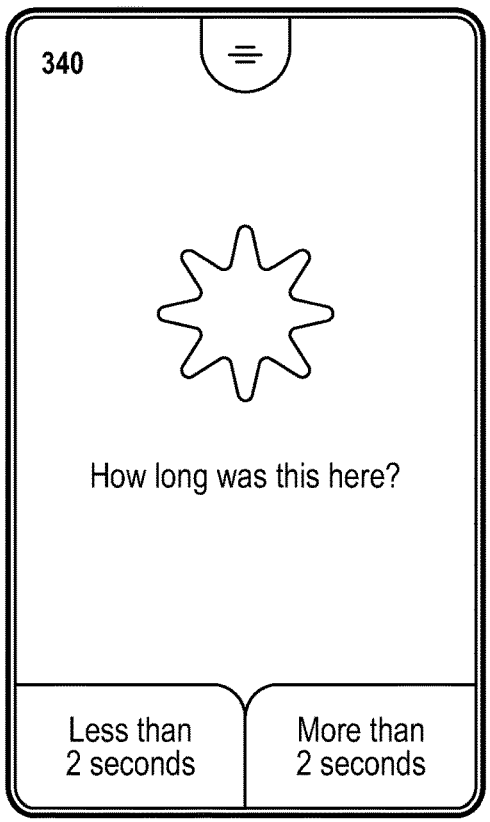
Figure 4D:
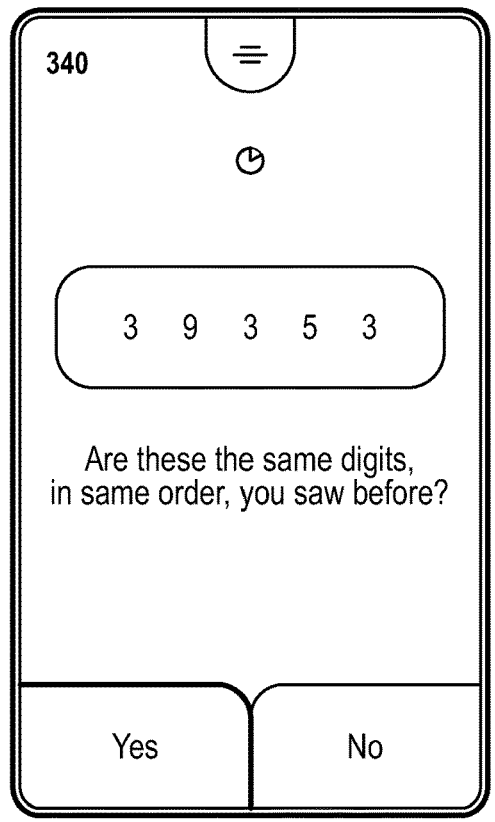
Figure 5A:
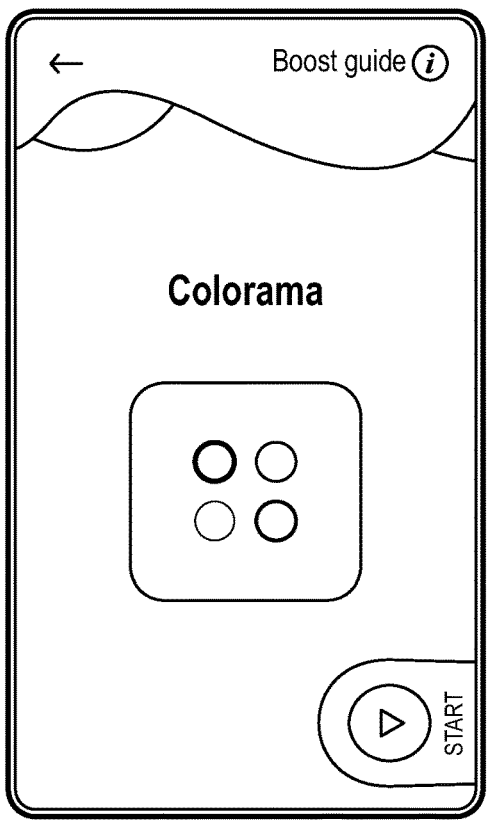
FIGS. 5A through 5D are screen shots of an example of a colorama game that provides a moderate cognitive load, in accordance with some implementations of the present disclosure.
Figure 5B:
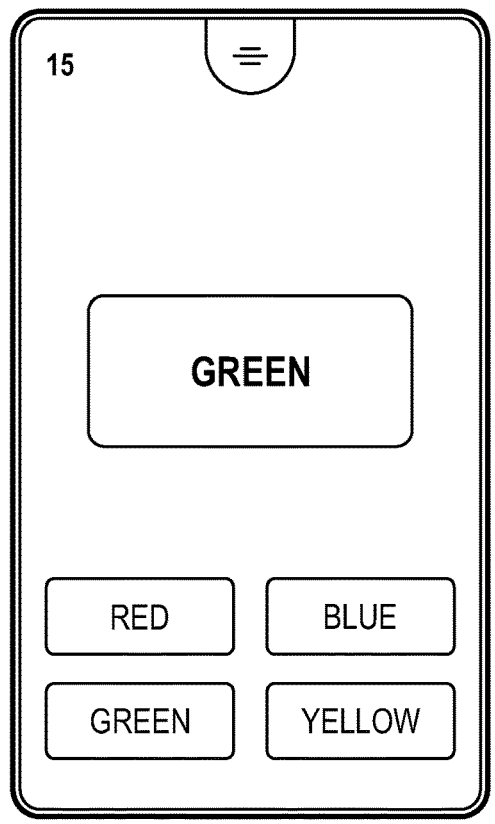
Figure 5C:
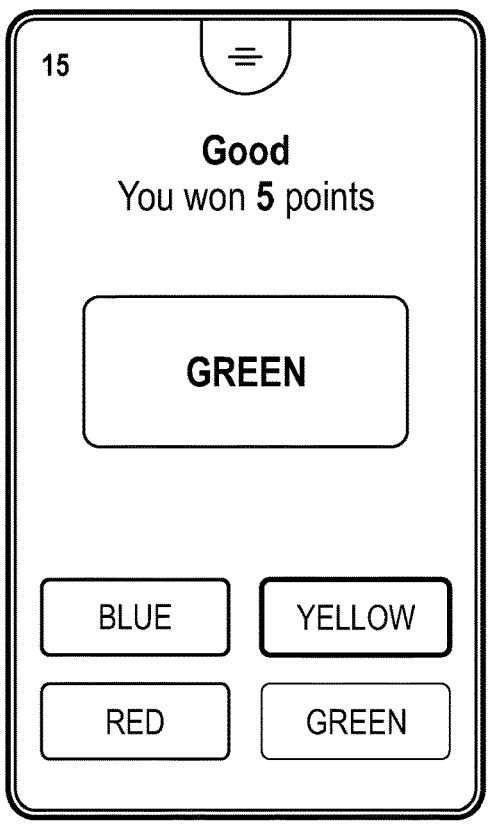
Figure 5D:
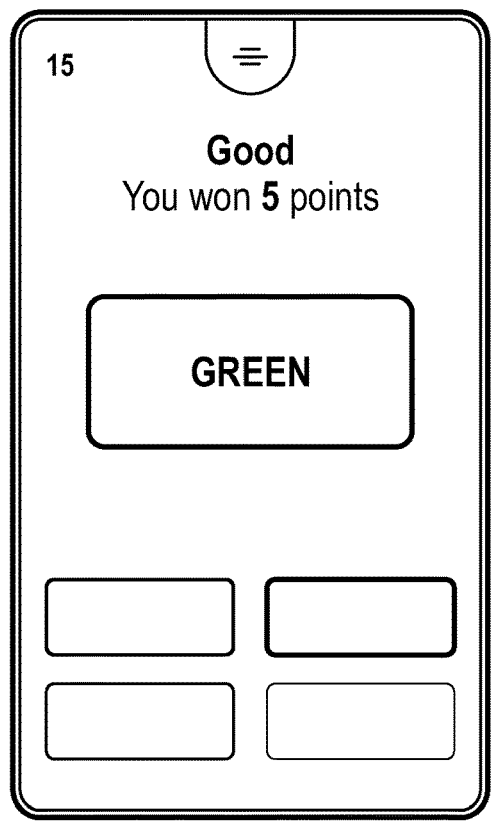
Figure 6A:
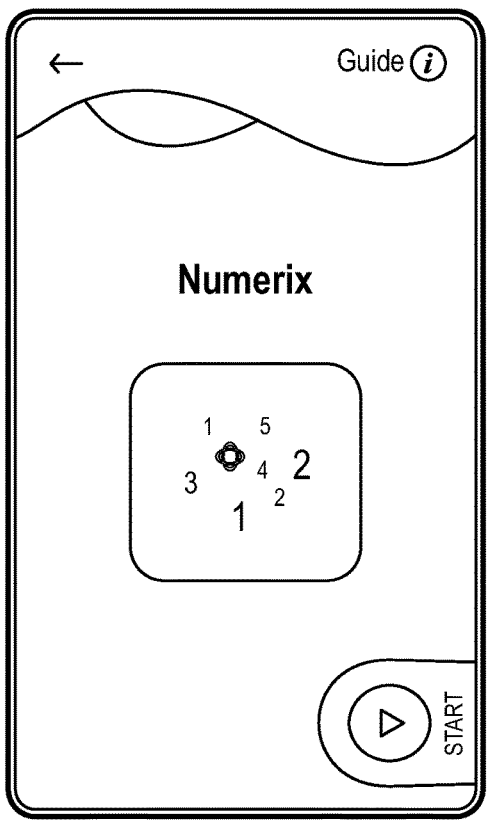
FIGS. 6A through 6D are screen shots of an example of a numerix game that provides a moderate cognitive load, in accordance with some implementations of the present disclosure.
Figure 6B:
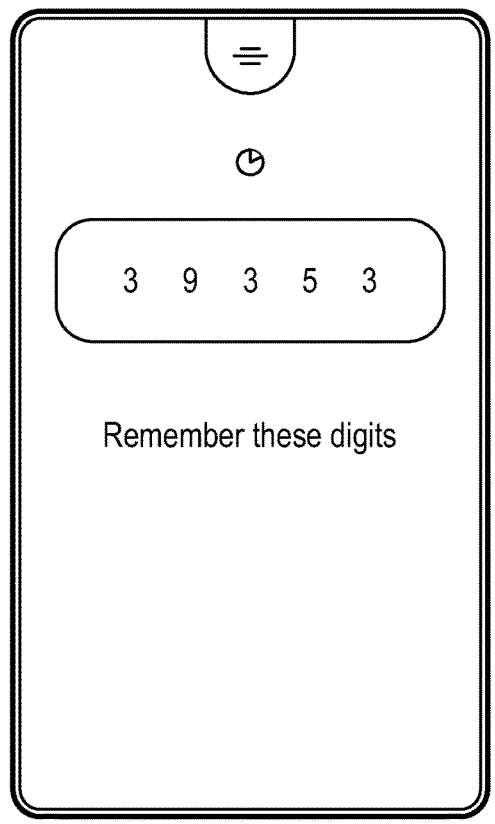
Figure 6C:
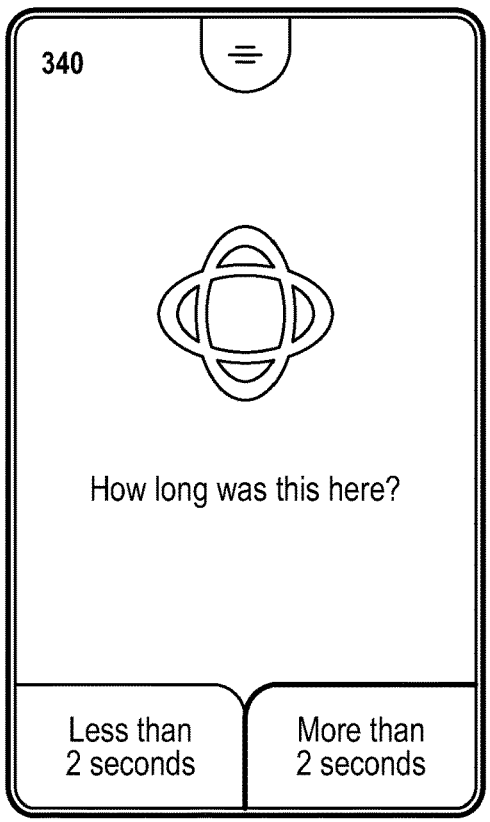
Figure 6D:
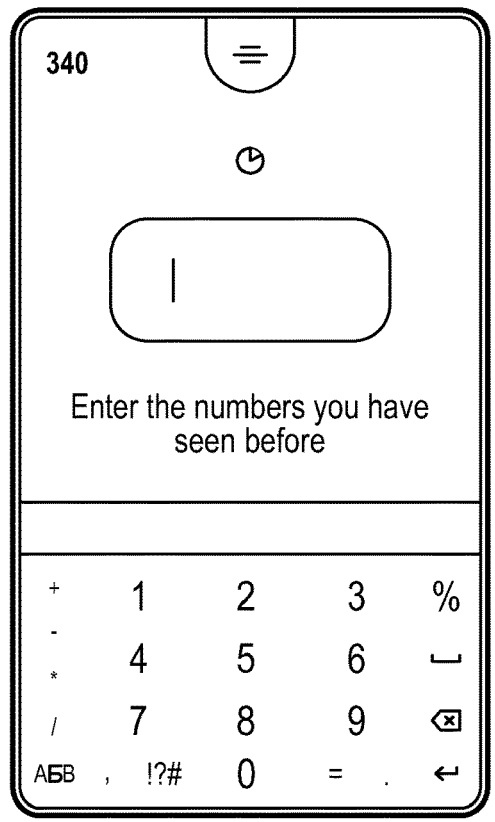
Figure 7A:
FIGS. 7A through 7D are screen shots of an example of a golf game that provides a high cognitive load, in accordance with some implementations of the present disclosure.
Figure 7B:
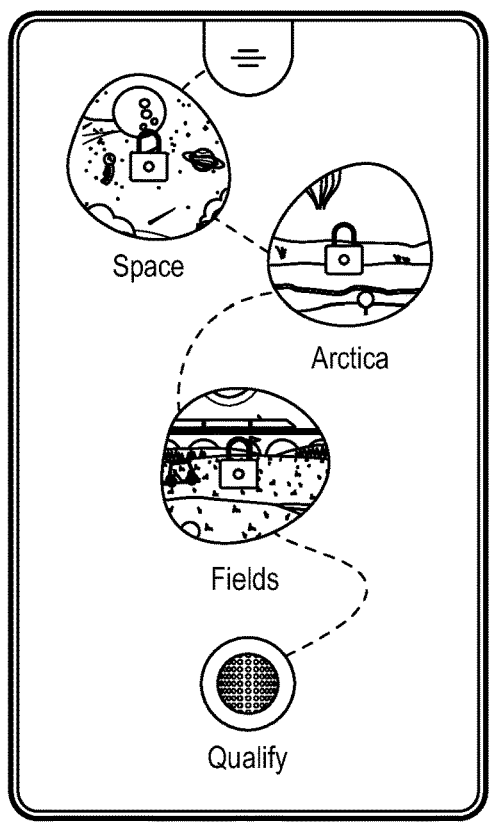
Figure 7C:
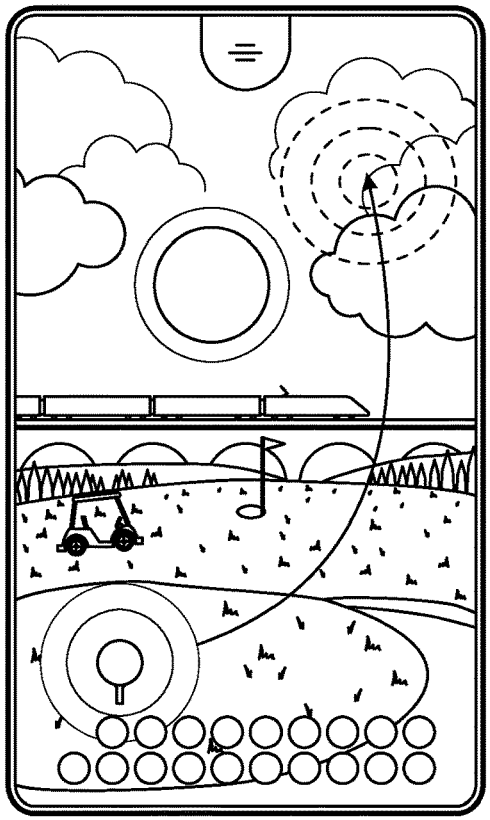
Figure 7D:
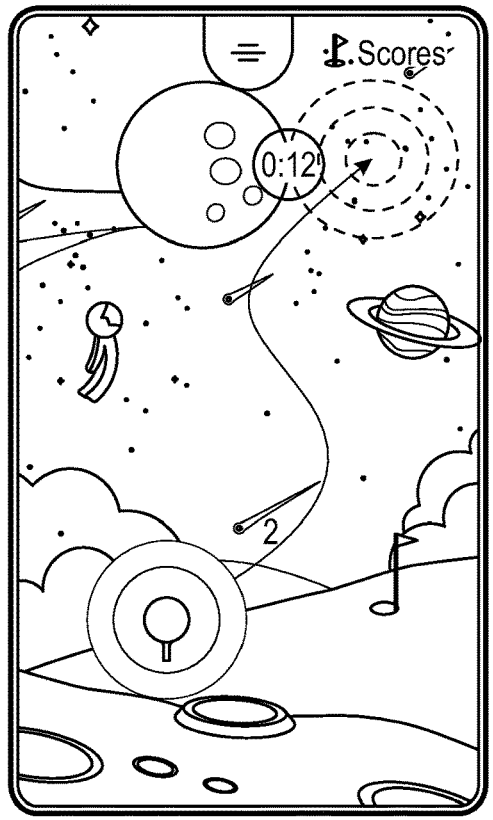
Figure 8A:
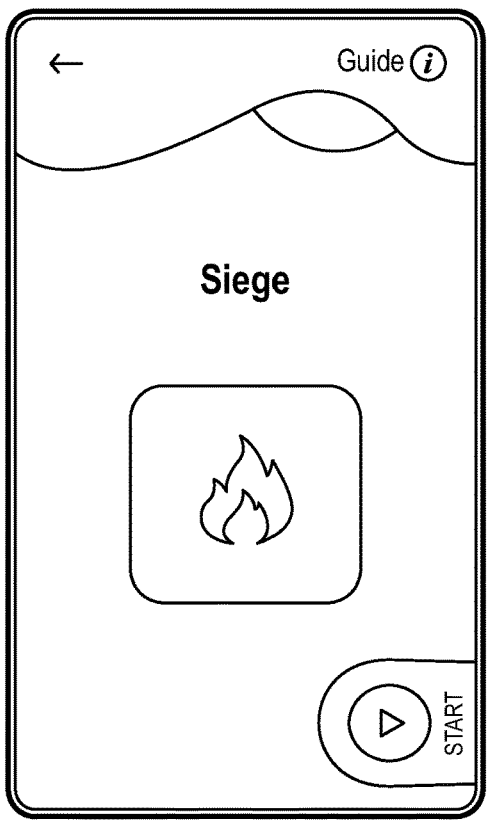
FIGS. 8A through 8D are screen shots of an example of a siege game that provides a high cognitive load, in accordance with some implementations of the present disclosure.
Figure 8B:
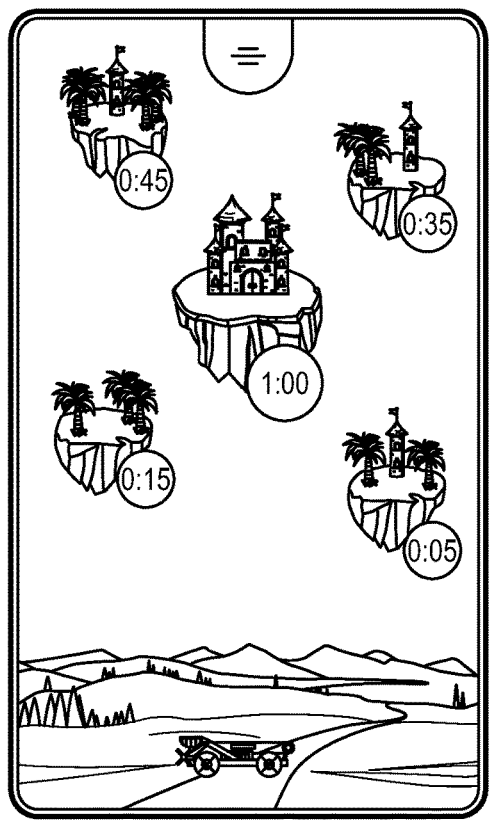
Figure 8C:
Figure 8D:

One or more of the boost games are configured to provide moderate cognitive loads to facilitate self-control training. Boost games configured to provide moderate cognitive loads are sometimes referred to herein as "stage two boost games." Stage two boost games are configured to target the cognitive processes of working memory, procedural memory, ecological assessment, cognitive flexibility, choice-making, or a combination thereof. For example, FIGS. 3A through 3D are screen shots of a match game that provides a moderate cognitive load. In some implementations, the match game is a gamified version of the Wisconsin Card Sorting Test™. For example, through trial and error, a user locates a paired match between a stimulus card and one of plurality of response cards. In some implementations, each trial of the match game includes four response cards, as illustrated in FIGS. 3C and 3D. The matching patterns may include, for example, color, shape, number, or a combination thereof. In some implementations, the matching patterns are randomly changed after the few trials. In some implementations, the match game provides bonus points for rapid and consecutive correct answers.

FIGS. 4A through 4D are screen shots of a digits game that provides a moderate cognitive load. The digits game is a memorization game. In some implementations, the digits game includes a gamified version of the Concurrent Digit Span Test. For example, the main objective of the digits game may be to remember a set of numbers and, after a short time interval, guess whether the set of numbers shown is the same as shown earlier. In some implementations, the digits game may include a secondary task that provides bonus points when the user correctly guesses the duration of the short time interval. In some implementations, the digits game may include one or more intermediate pauses or one or more requirements to recall an additional shape or number, in a nested fashion. In some implementations, the digits game includes the presentation and recollection of shapes, colors, sounds, or a combination thereof.

FIGS. 5A through 5D are screen shots of a colorama game that provides a moderate cognitive load. In some implementations, the colorama game includes a gamified version of the Stroop Test. For example, a user may be tasked with finding a match between a color in which a word is written on a stimulus card and one of the plurality of response cards naming this color. For example, in FIG. 5B, the word written on the stimulus card is colored red. Thus, the correct match in this example is the response card labelled "RED." In some implementations, the colorama game provides additional points for fast and consecutive correct responses. In some implementations, the colorama game may progress in complexity with additional card design variations.

FIGS. 6A through 6D are screen shots of a numerix game that provides a moderate cognitive load. The numerix game is a memorization game. In some implementations, the numerix game includes a gamified version of the Concurrent Digital Span Test. For example, the main objective of the numerix game may be to remember a set of numbers and recall the set of numbers after a short time interval.

One or more of the plurality of boost games are configured to provide high cognitive loads to facilitate additional self-control training. Boost games configured to provide high cognitive loads are sometime referred to herein as "stage three boost games." Stage three boost games are configured to target the cognitive processes of time perception (sometimes referred to as "timing accuracy"), inhibitory control, delay tolerance, mindfulness, episodic future thinking, plan making, or a combination thereof. FIGS. 7A through 7D are screen shots of a golf game that provides a high cognitive load. The golf game is a time perception and delay training game in which gameplay is focused on pacing actions in target time periods (for example, seconds to minutes). The golf game is styled as a golf simulator, wherein the accuracy of each golf shot depends on the accuracy of user input for a target time period. In some implementations, a user may depress a point on a screen for a target time period to make a golf shot. Alternatively, or in addition, a user may move their finger along a predetermined path on the screen for a target time period to make a golf shot. No visual indication of the passage of time is displayed during the golf game. For example, no device clock is visible on-screen. Further, in order to avoid presenting the user with an implicit clock by which timing may be estimated, no predictably repeating animation patterns are displayed on the screen. In some implementations, the user is periodically instructed within the golf game to avoid counting out loud or in their mind (i.e., non-verbally) to the extent possible. After each golf shot, the user is informed about the timing accuracy of the golf shot. For example, a score may be determined based on the accuracy above or below the target time period. In some implementations, trial difficulty (for example, acceptable thresholds for deviation from the target time period) may be adjusted based on the user's trailing performance. As the user progresses, new levels of the golf game may be unlocked, with more challenging target time periods and changed appearance.

FIGS. 8A through 8D are screen shots of a siege game that provides a high cognitive load. The siege game is a time perception game that incorporates a vigilance test. For example, gameplay in the siege game is focused on pacing actions in target time intervals, including multi-layered distractions and additional timing challenges. The siege game is configured as a multi-level adventure in which a user guides a catapult across a landscape and destroys enemy castles in a given area. After a start signal is displayed, a user may press on the catapult to start movement towards a castle. In some implementations, the reaction time of the user is recorded as a vigilance score. For example, the time between the initial display of the start signal and the initiation of activity by the user may be recorded. As the user navigates the catapult through a series of obstacles and distraction courses, the user is reported for avoiding these obstacles or navigating through a plurality predetermined paths correctly. The user is instructed to release the catapult after a target time interval to fire a shot at a castle. The target time period may be, for example, between 5 seconds and 120 seconds. The user is instructed to correctly time the release of the catapult after the target time interval without relying on clocks or external aids. The closer the user's pressing time is to the target time period, the more damage is done to the castle. After each shot, the user is informed about their timing accuracy and their rate of successful avoidance of obstacles, each resulting in a multi-factor points score. The multi-factor points score (reflecting timing accuracy, vigilance, and obstacle avoidance) may lead to differing levels of destruction of the castle. In some implementations, multiple trials may be required to destroy the castle. After the complete destruction of castle, the user may progress to a different level, for example, with a longer target time period. In some implementations, after all castles in a given area are destroyed, more challenging levels are unlocked with different appearances of, for example, environment, obstacles, castles, or a combination thereof.

Figure 9:
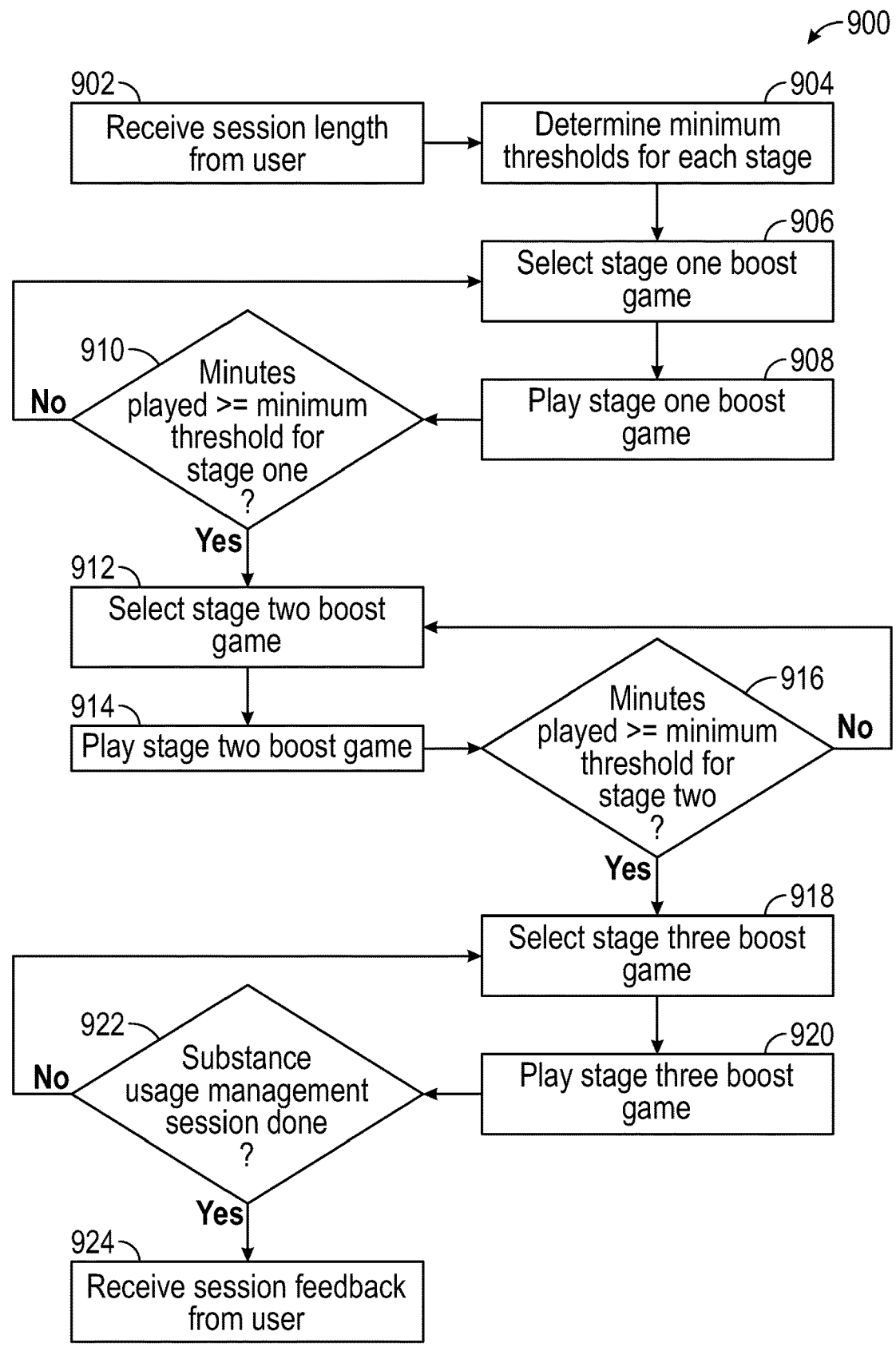
FIG. 9 is a flow diagram of an example of a substance usage management session, in accordance with some implementations of the present disclosure.

FIG. 9 is a flow diagram of an example of a substance usage management session 900. As described in more detail below, the substance usage management session 900 provides a user with a combination of boost games with low, moderate, and high cognitive loads to shift a user's selective attention away from their internal qualia and deliver brief sessions of self-control training. A user may use the substance usage management session 900 to delay taking a scheduled dose of a substance. Further, a user may use the substance usage management session 900 to manage a substance craving that the user is currently experiencing. Substance cravings may include, for example, drug cravings (both prescription and illegal drugs), food cravings, and alcohol cravings. Thus, the substance usage management session 900 may provide, among other thing, a just in time intervention to a user during a substance craving. For example, the structured presentation of information relating to experiential qualia, such as the projected passage of time, may constitute an asynchronous reinforcement form of self-control training as it brings awareness to implicit biases in estimation that are often greater in individuals with addiction and other mental health disorders related to impulsivity.

The substance usage management session 900 is performed by processing logic that may include hardware (circuitry, dedicated logic, etc.), software (such as is run on a general-purpose computer system, a dedicated machine, or a computing device of any kind (for example, IoT node, wearable, smartphone, mobile device, etc.)), or a combination of both. The substance usage management session 900 and/or each of its individual functions (including "methods," as used in object-oriented programming), routines, subroutines, or operations may be performed by one or more processors of a computing device (for example, any component of FIG. 17, as will be described below). In certain implementations, the substance usage management session 900 may be performed by a single processing thread. Alternatively, the substance usage management session 900 may be performed by two or more processing threads, wherein each thread implements one or more individual functions, routines, subroutines, or operations of the substance usage management session 900.

For simplicity of explanation, the substance usage management session 900 is depicted in FIG. 9 and described as a series of operations performed by a smartphone. However, operations in accordance with the present disclosure can occur in various orders and/or concurrently, and/or with other operations not presented and described herein. For example, the operations depicted in the substance usage management session 900 in FIG. 9 may occur in combination with any other operation of any method disclosed herein. Furthermore, not all illustrated operations may be required to implement the substance usage management session 900 in accordance with the disclosed subject matter. In addition, those skilled in the art will understand and appreciate that the substance usage management session 900 could alternatively be represented via a state diagram or event diagram as a series of interrelated states.

Figure 10A:
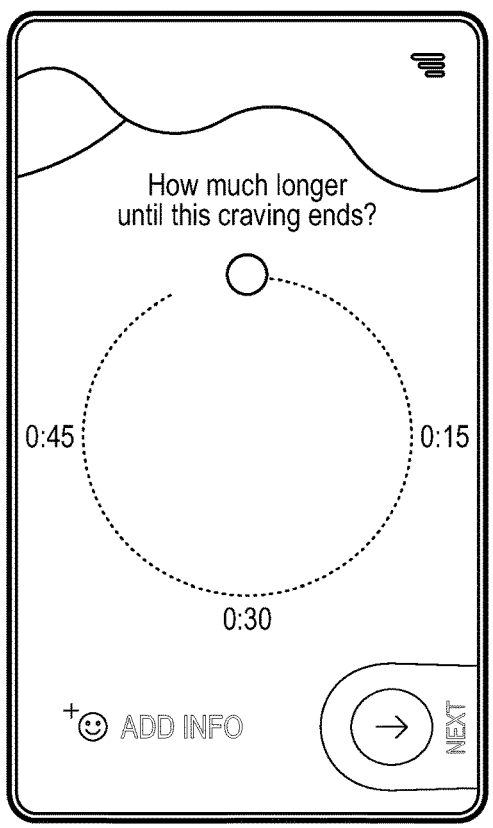
FIGS. 10A and 10B are screen shots of an example of a graphical user interface for providing a substance craving duration, in accordance with some implementations of the present disclosure.
Figure 10B:
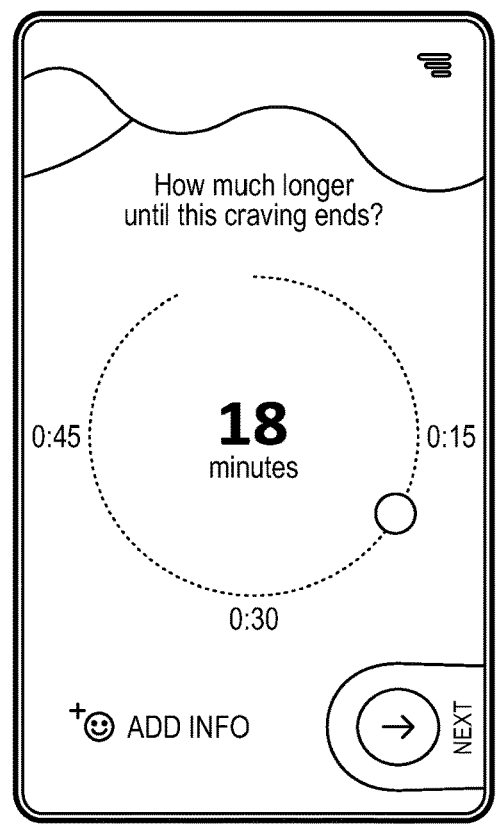

At block 902, a session length is received from a user. In some implementations, the session length may include a dose delay duration representing the amount of time that the user wants to delay taking a scheduled (or recommended) dose of a substance. Alternatively, or in addition, the session length may include a substance craving duration representing the amount of time that the user estimates a current substance craving will last. In general, a drug craving usually lasts between five minutes and fifteen minutes. However, a drug craving can last for a longer time period such as an hour. In some implementations, a smartphone may display a visual prompt to the user requesting an estimated (projected) substance craving duration. For example, FIG. 10A is a screen shot of a graphical user interface prompting a user to provide the substance craving duration. In the example illustrated, the user slides a selection point along a round-shaped timescale to select the substance craving duration. For example, as illustrated in FIG. 10B, the selection point is slid along the round-shaped timescale to select a substance craving duration of eighteen minutes.

Returning to FIG. 9, at block 904, minimum thresholds are determined for three stages of boost games. The substance usage management session 900 is described as including three stages. However, alternate implementations of the substance usage management session 900 may include fewer than three stages or more than three stages. In some implementations, the minimum threshold for a stage indicates the minimum number of minutes that boost games from that stage should be played before changing to boost games from a higher stage. For example, a minimum threshold of five minutes for the first stage may indicate that the user should play stage one boost games for at least five minutes before playing stage two boost games. Alternatively, or in addition, the minimum threshold for a stage may indicate the minimum number of intervals, turns, or rounds of boost games from that stage that should be played before changing to boost games from a higher stage. For example, a minimum threshold of three turns for the second stage may indicate that the user should play three turns of stage two boost games before playing stage three boost games.

The minimum thresholds for each of the three stages are determined based on the session length. In some implementations, the minimum thresholds for each of the three stages are determined by dividing the session length into three equal time durations. For example, for a session length of fifteen minutes, the minimum threshold for each of the three stages may be set to five minutes. Alternatively, or in addition, the minimum thresholds for each of the three stages are determined by dividing the session length into three unequal time durations. For example, one or more of the three stages may receive a larger portion of the session length than the other stages. As a specific example, for a session length of ten minutes, the minimum thresholds for stages one and two may both be set to four minutes and the minimum threshold for stage three may be set to two minutes. Alternatively, or in addition, the minimum thresholds for each of the three stages are determined to ensure that each minimum threshold is greater than or equal to predetermined minimum values. For example, stage one may require a minimum of two minutes in order to complete an interval. Thus, regardless of the session length, the minimum threshold for stage one is set to at least two minutes. The predetermined minimum values for each stage may be the same values or different values.

Figure 11A:
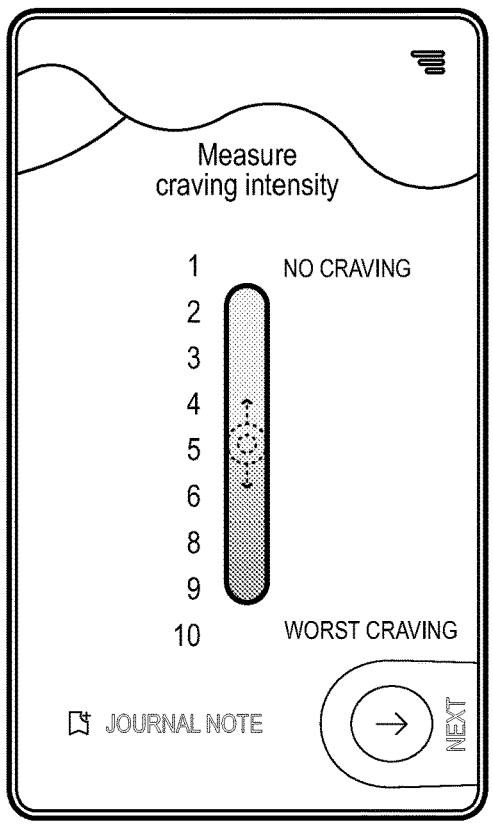
FIGS. 11A and 11B are screen shots of an example of a graphical user interface for providing a substance craving intensity, in accordance with some implementations of the present disclosure.
Figure 11B:
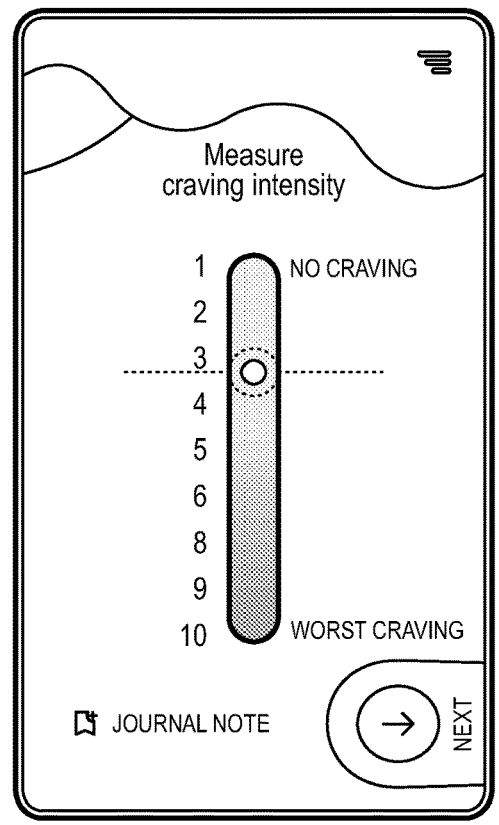

In some implementations, the minimum thresholds for each of the three stages may further be determined based in part on a user pain level representing an indication of how much pain the user is currently experiencing or has previously experienced. Alternatively, or in addition, the minimum thresholds for each of the three stages may further be determined based in part on a substance craving intensity representing an indication of how intense the substance craving is or has previously been. For example, FIG. 11A is a screen shot of a graphical user interface prompting a user to provide a substance craving intensity. In the example illustrated, the user slides a selection point along a vertical intensity scale to select the substance craving intensity. For example, as illustrated in FIG. 11B, the selection point is slid along the vertical intensity scale to select a substance craving intensity of three and a half.

In some implementations, the minimum thresholds for each of the three stages may further be determined based in part on one or more other attributes of the user. Attributes of the user may include, for example, pupillary size, skin temperature, heart rate, heart rate variability, photoplethysmography arterial oxygen saturation (PPG SpO2), galvanic skin response (for example, the presence of skin sweat and its chemical constituents, or electrodermal activity patterns), voice stress, relative body acceleration or body limb positioning, information pertaining to an age of the user, information pertaining to a gender of the user, an indication of a mental state of the user, information pertaining to a genetic condition of the user, information pertaining to a disease state of the user, an indication of an energy level of the user, information pertaining to a weight of the user, information pertaining to a height of the user, information pertaining to a body mass index of the user, information pertaining to a family medical history of the user, information pertaining to comorbidities of the user, or some combination thereof. User attributes may be measured, for example, by a smartphone camera, smartphone microphone, or a smartphone-connected wearable sensor. Attributes of the user may be processed by the substance usage management system to determine, for example, craving, pain, and cognitive load.

Returning to FIG. 9, at block 906, a stage one boost game is selected. In some implementations, the stage one boost game is selected via a pseudorandom process. For example, a pseudorandom number generator may select a number that is associated with one of a plurality of stage one boost games. Alternatively, or in addition, the stage one boost game is selected based on one or more attributes of the user (including any of the attributes described herein). Alternatively, or in addition, the stage one boost game is selected based on historical usage data. For example, the dots game may be selected as the stage one boost game if the user struggled to complete the shapes game during a previous substance usage management session.

At block 908, the selected stage one boost game is played. For example, an interval or round of the selected stage one boost is played. As a more specific example, when the shapes game is selected, a set of polygons and a square gridded board are displayed and the game continues until the user finds the correct placement for each of the set of polygons to fit into the square gridded board.

At block 910, the smartphone determines whether the minutes played is greater or equal to the minimum threshold for stage one. When the minutes played is less than the minimum threshold for stage one, the substance usage management session 900 returns to block 906 to select a stage one boost game again. In some implementations, a different stage one boost game may be selected. For example, when the performance of the user in the stage one boost game at block 908 is less than a predetermined threshold, the previously-selected stage one boost game may be too difficult for the user and a different stage one boost game is selected. Alternatively, or in addition, the same stage one boost game may be selected again. In some implementations, when the same stage one boost game is selected again, one or more parameters of the stage one boost game are adjusted. For example, when the performance of the user in the stage one boost game at block 908 is greater than a predetermined threshold, the previously-selected stage one boost game may be too easy for the user and the difficulty of the stage one boost game may be increased. The stage one boost game may be made increasingly difficult through adjustment of interaction parameters, such that the stage one boost game has an incrementally elevated cognitive load. Alternatively, or in addition, the stage one boost game may be made increasingly difficult through adjustment of the game scoring system (for example, a percentile scoring schedule or a trailing average schedule), such that rewards are accumulated at a diminished level for otherwise equivalent performance.

Returning to block 910, when the minutes played is greater than or equal to the minimum threshold for stage one, a stage two boost game is selected at block 912. The stage two boost game may be selected using any of the methods described above in relation to block 906 for selecting the stage one boost game. Alternatively, or in addition, the stage two boost game may be selected based on the user's performance while playing the stage one boost game at block 908. Alternatively, or in addition, the stage two boost game may be selected based on one or more attributes of the user (including any of the attributes described herein).

At block 914, the selected stage two boost game is played. Next, at block 916, the smartphone determines whether the minutes played is greater or equal to the minimum threshold for stage two. When the minutes played is less than the minimum threshold for stage two, the substance usage management session 900 returns to block 912 to select a stage two boost game again. Alternatively, when the minutes played is greater than or equal to the minimum threshold for stage two, a stage three boost game is selected at block 918. The stage three boost game may be selected using any of the methods described above in relation to block 906 for selecting the stage one boost game. Alternatively, or in addition, the stage three boost game may be selected based on the user's performance while playing the stage one boost game at block 908, the stage two boost game at block 914, or both. Alternatively, or in addition, the stage three boost game may be selected based on one or more attributes of the user (including any of the attributes described herein).

At block 920, the selected stage three boost game is played. Next, at block 922, the smartphone determines whether the substance usage management session 900 is done. In some implementations, the smartphone may determine that the substance usage management session 900 is done when the minutes played is greater than or equal to the minimum threshold for stage three. Alternatively, or in addition, the smartphone may determine that the substance usage management session 900 is done when the minutes played is greater than or equal to the session length. Alternatively, or in addition, the smartphone may prompt the user to indicate whether the substance usage management session 900 is done. For example, when the substance usage management session 900 is being used to address a substance craving of a user, the smartphone may display a prompt to the user asking whether their substance caving has abated. When not done, the substance usage management session 900 returns to block 918 to select a stage three boost game again. Alternatively, when the substance usage management session 900 is done, session feedback is received from the user at block 924. In some implementations, the session feedback may include an indication of how intense the substance craving was (for example, the substance craving intensity described above). Session data (for example, date, location, other smartphone-derived metadata, user-provided qualia, perceived craving trigger, and boost game performance and rewards measures) is recorded in the substance usage management platform and may be available for later display to the user or a healthcare professional in a form such as a cravings log, an entry in a journal, or in a performance dashboard. In some implementations, the user may append session entries in an electronic journal, for example, for either cravings events or for dose administration events, including capability for additional text notation, voice messages, phonographs, smartphone-derived metadata, and other user-generated content to be added as records for later review.

In some implementations, the substance usage management platform described herein include check-in sessions with the user. Check-in sessions may be performed periodically. For example, check-in sessions may be performed weekly, bi-weekly, or monthly. Check-in sessions may also be performed on-demand. For example, a check-in session may be requested by the user when the user is not currently experiencing a substance craving. Check-in sessions are baseline gatherings of surveys and other instruments that may be used to calibrate boost game selection, as well as other things, some of which are described in more detail below. Check-in sessions may include one or more psychometric assessments to evaluate real-time impulsive choice, working memory, timing ability, inhibitory control, delay tolerance related to momentary self-control, or a combination thereof. Check-in sessions may also include a self-confidence or self-efficacy measure (for example, the Treatment Effectiveness Assessment). Check-in sessions may also include a gamified version of the hypothetical impulse control task. The hypothetical impulse control task assesses impulsive choices for hypothetical rewards such as food (for example, candy) after delays of five seconds to thirty seconds. Check-in sessions may also include a gamified version of the Monetary Choice Questionnaire Task. The Monetary Choice Questionnaire Task is a twenty-seven question survey including questions such as "Would you rather have $14 now or $25 in 19 days?" Check-in sessions may also include retrospective self-reports of craving event qualia (for example, craving event frequency, intensity, duration, and overall functional impairment burden) as measured on a Likert scale or visual analog scale, and other instruments (for example, a desire for substances questionnaire and a substance craving scale), and other comments or notations relevant for treatment planning (for example, ecological assessments of substance usage patterns and triggers, or user estimates of propensity of substance use in the prior and forthcoming time periods). Check-in sessions may include other questionnaires such as the Internal Inhibition Scale, the PSQ-9, and the Pain Severity Index.

Figure 12:
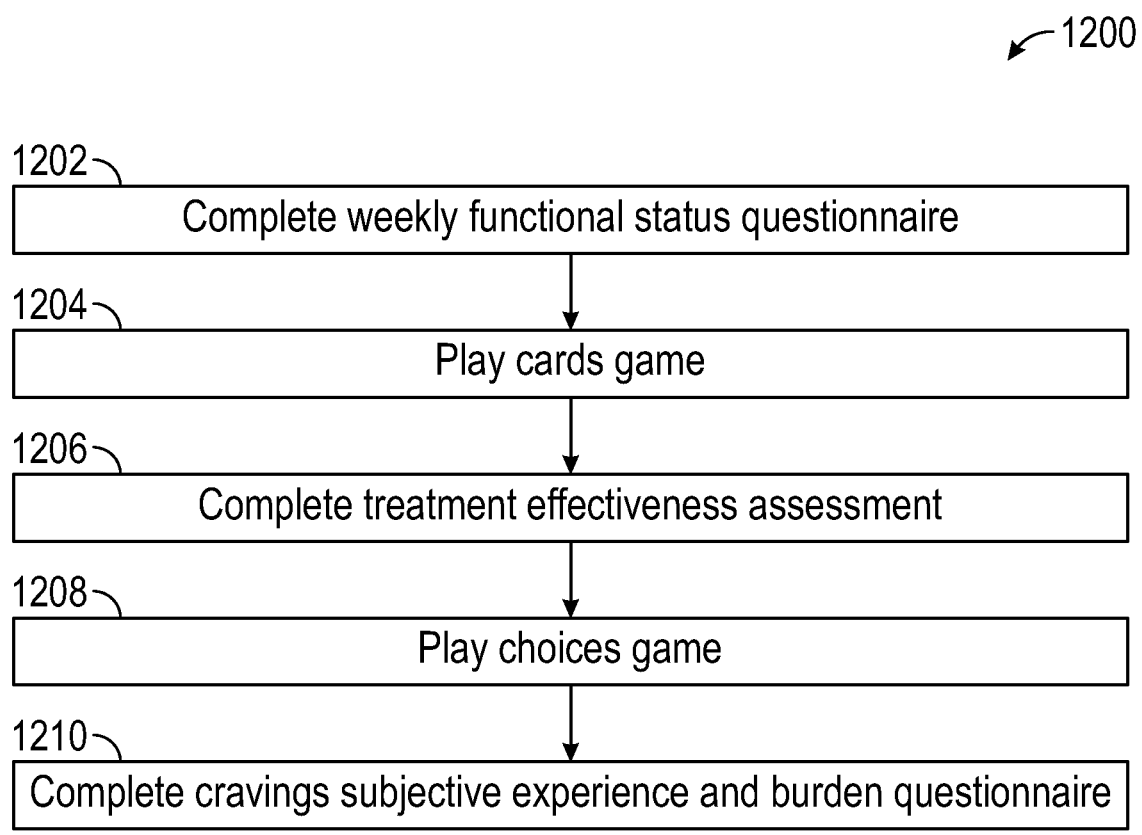
FIG. 12 is a flow diagram of an example of a check-in session with a user, in accordance with some implementations of the present disclosure.
Figure 13A:
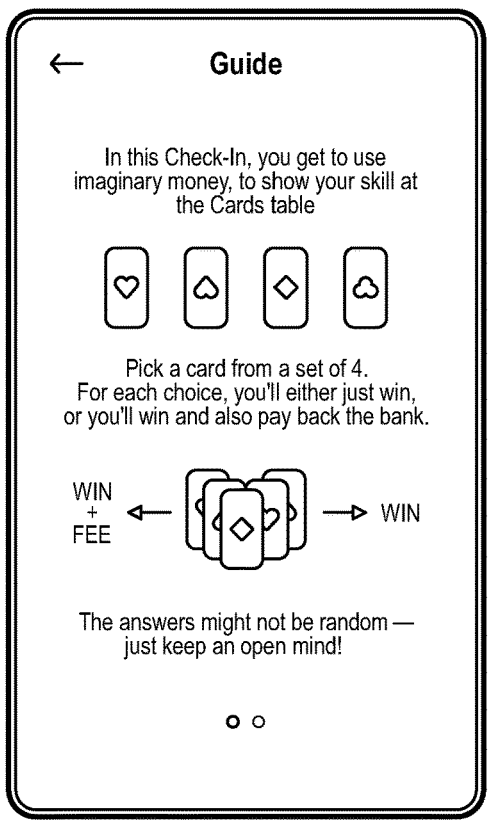
FIGS. 13A through 13D are screen shots of an example of a cards game used in a check-in session, in accordance with some implementations of the present disclosure.
Figure 13B:
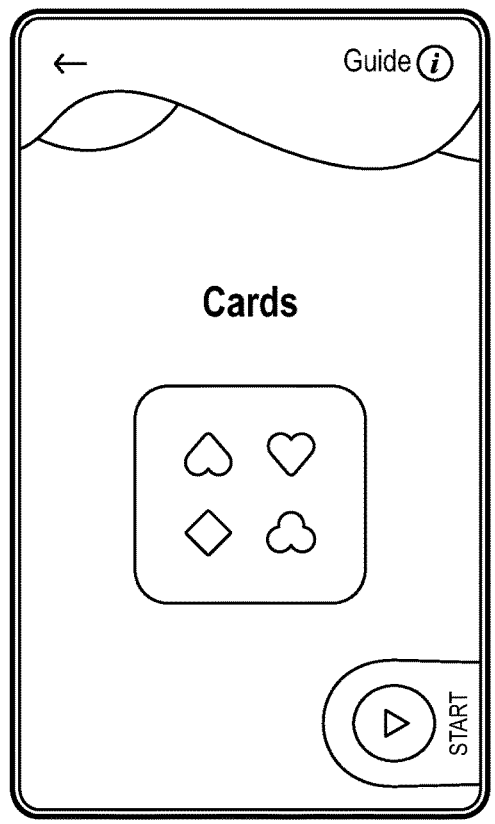
Figure 13C:
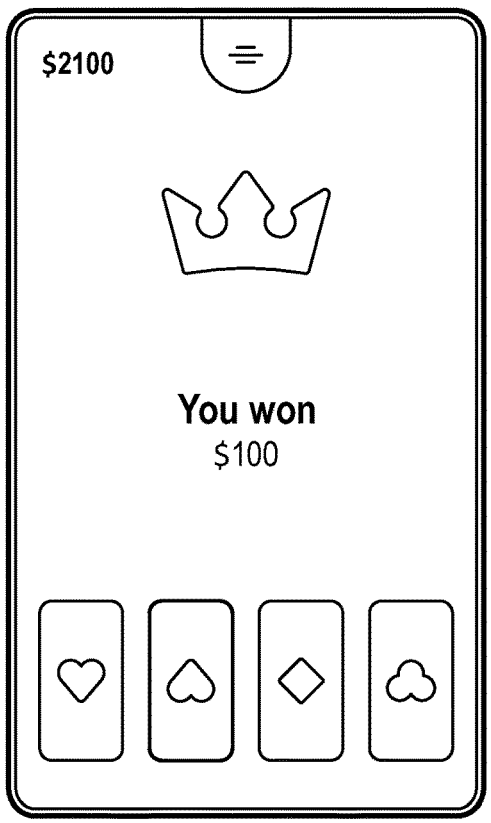
Figure 13D:
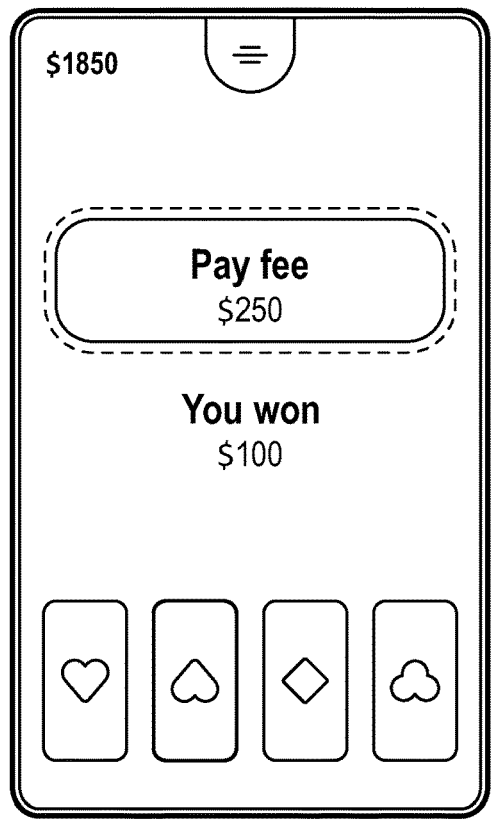

FIG. 12 is a flow diagram of an example of a check-in session 1200 with a user. The check-in session 1200 is performed by processing logic that may include hardware (circuitry, dedicated logic, etc.), software (such as is run on a general-purpose computer system, a dedicated machine, or a computing device of any kind (for example, IoT node, wearable, smartphone, mobile device, etc.)), or a combination of both. The check-in session 1200 and/or each of its individual functions (including "methods," as used in object-oriented programming), routines, subroutines, or operations may be performed by one or more processors of a computing device (for example, any component of FIG. 17, as will be described below).

For simplicity of explanation, the check-in session 1200 is depicted in FIG. 12 and described as a series of operations performed by a smartphone. However, operations in accordance with the present disclosure can occur in various orders and/or concurrently, and/or with other operations not presented and described herein. For example, the operations depicted in the check-in session 1200 in FIG. 12 may occur in combination with any other operation of any method disclosed herein. Furthermore, not all illustrated operations may be required to implement the check-in session 1200 in accordance with the disclosed subject matter. In addition, those skilled in the art will understand and appreciate that the check-in session 1200 could alternatively be represented via a state diagram or event diagram as a series of interrelated states.

At block 1202, a weekly functional status questionnaire is completed by the user. For example, a smartphone may display questions to a user and the user inputs responses. At block 1204, a cards game is played. The cards game is a gamified version of the Iowa Gambling Task. FIGS. 13A through 13D are screen shots of an example of the cards game. As illustrated in FIGS. 13A through 13D, the user is presented with four decks of cards. Each deck holds cards that will either reward or penalize the user using game money. The goal of the cards game is to win as much money as possible. The decks may differ from each other in the balance of reward cards versus penalty cards. Thus, some decks are bad decks, and other decks are good decks because some decks will tend to reward the user more often than other decks. The user is not told that the two bad decks have larger rewards, but also larger or more frequent penalties. On balance, the penalties in the bad decks outweigh the higher rewards they give. Therefore, the user should choose the decks with smaller rewards as they will also give significantly fewer penalties and give a better long-term payout. In some implementations, the user is additionally rewarded points for having a final game money score that is greater than or equal to a threshold value.

Returning to FIG. 12, at block 1206, the Treatment Effectiveness Assessment is completed by the user. At block 1208, a choices game is played. The choices games is a variation of the Kirby Delay-Discounting Task. FIGS. 14A through 14D are screen shots of an example of the choices game. In the choices game, the user completes a series of questions that require choosing between a smaller, immediate reward and a larger, later reward. For example, at illustrated in FIG. 14C, the user may choose either to receive $35 now or to receive $89 in one hundred days. Returning to FIG. 12, at block 1210, a cravings subjective experience and burden questionnaire is completed by the user. In some implementations, data of the types shown in block 1202, block 1206, and block 1210 may be collated and combined with boost game data and other session data, and transformed, in cross section or in a trend-based algorithm, for the purposes of creating a user profile (score) which indicates relative self-control or self-efficacy.

In addition to boost game selection, check-in sessions may be used to calibrate parameters of boost games. For example, returning briefly to FIG. 9, after a boost game is selected at block 906, block 912, or block 918, parameters of the selected boost game may be adjusted. In some implementations, parameters of the selected boost game are adjusted based on trailing performance within the current substance usage management session. For example, the difficulty of a selected boost game may be adjusted based on trailing performance of the user within the selected boost game or across different boost games played during the current substance usage management session. Alternatively or in addition, parameters of boost games are adjusted based on baseline user measurements derived, for example, from check-in sessions, historical usage patterns, aggregated boost psychometric performance data, or a combination thereof.

In some implementations, the substance usage management platform adjusts one or more parameters of the boost games based on a user state determined prior to a substance usage management session. The user state may include, for example, a psychometric profile of the user and biometric information of the user. The user state may also include a chronotype of the user. One or more parameters of the boost games may vary based on the chronotype of the user. For example, parameter X of a boost game may vary based on the chronotype of the user. In some implementations, a healthcare professional may specify a chronotype for the user (for example, Morning Type (M Type) and Evening Type (E Type), or Neither Type (N Type)). In some implementations, the substance usage management platform determines a chronotype from biometric information or user psychometric profile data (for example, as collected from a Circadian Type Questionnaire (CTQ), Morningness-Eveningness Questionnaire (MEQ), Munich Chronotype Questionnaire (MCTQ), or Morningness-Eveningness-Stability-Scale (MESS)).

The user state may also include a circadian rhythm phase of the user. Circadian rhythm is a regular time sequence with influence in the regulation of biologic functions under a periodicity of approximately twenty-four hours in normal humans, which may be characterized by one or more time-varying or fixed parameters and components. Circadian cycles may include identifiable circadian rhythm phases (also known as circadian phases, circadian timing periods, or circadian cycle points), of minutes to hours duration. Circadian rhythm phases may include one or more waveform parameters, for example, acrophase, Midline Estimating Statistic of Rhythm (MESOR), or amplitude. One or more parameters of the boost games may vary based on the circadian rhythm phase of the user. For example, parameter X of a boost game may vary based on the circadian rhythm phase of the user. In some implementations, the substance usage management platform calculates Circadian rhythm phases using biometric information of the user (for example, using the Cosinor Method, a hidden Markov model, or the Dichotomy Index).

In some implementations, the substance usage management platform described herein includes a meta-game with a subset of boost games tied to a narrative or other theme. The meta-game uses points and adaptation to increase user engagement and psychological investment in completing boost games. For example, a user may accumulate rewards (for example, points) of a real or hypothetical nature by successfully completing boost games. Accumulated points of one or more types may be accumulated and subject to choice-making which results in increased point total accumulation. For example, boost games or the meta-game may offer the user a choice between spending points now to receive a small bonus or waiting for three more turns to spend points and receive a large bonus. Choice-making data is a form of diagnostic psychometric data and may be used by the system for calibration or score development. Choice-making data and other user interaction data may be used, in some implementations, to develop a user profile, indicating the psychological functioning and impulsivity level and self-control profile of the user. Points may be deployed within the meta-game by the user at specified periodic or randomly available intervals. For example, points may be used to allow the user to progress forward within the narrative or to adjust the parameters of boost games included in the meta-game. In some implementations, the meta-game may include metacognitive strategies to encourage the user to bank points. In some implementations, the meta-game or other components of the substance usage management platform may incorporate a function allowing the user to set goals for their personal lives, in the real world, by specifying a plurality of dates, goal types, and estimation data in response to prompts provided by the user interface, with the capability to record accomplished and deferred goals. In some implementations, the user may link the accumulation of hypothetical rewards (for example, points) in the substance usage management platform to the fulfillment of real rewards, or link the completion of the fulfillment of goals to the fulfillment of real rewards, which may be recorded by the substance usage management platform. Goal setting data may be used to as training data to configure the substance usage management platform.

Regarding adaptation, the parameters of boost games or the meta-game may be adjusted based on user selection, system selection, or both. Parameters of boost games or the meta-game may include, for example, interactive elements, gameplay elements, and scoring schedules. For example, the difficulty of boost games may be adjusted based on user preference, historical performance of the user (within or across different boost games), or both.

Figure 15A:
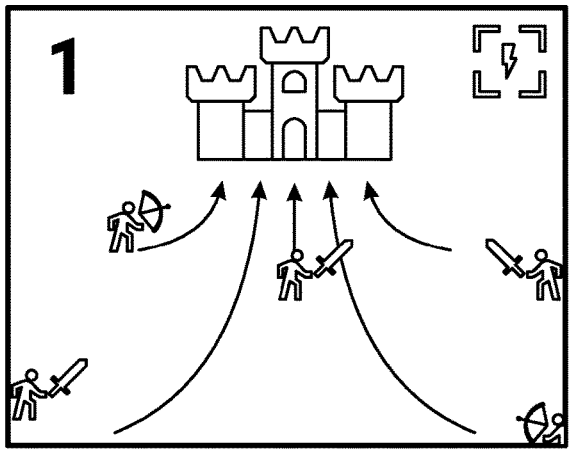
FIGS. 15A through 15D are screen shots of an example of a tower defense game, in accordance with some implementations of the present disclosure.
Figure 15B:
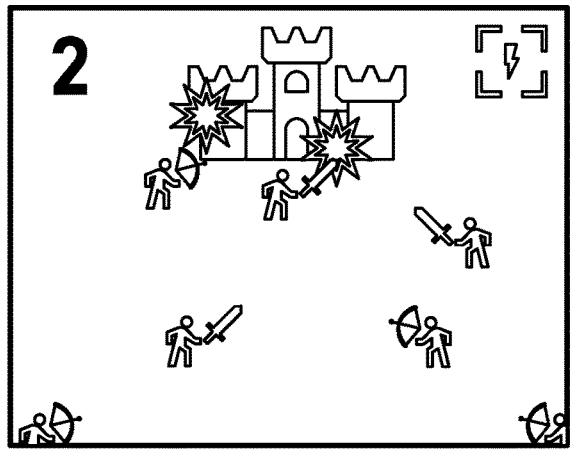
Figure 15C:
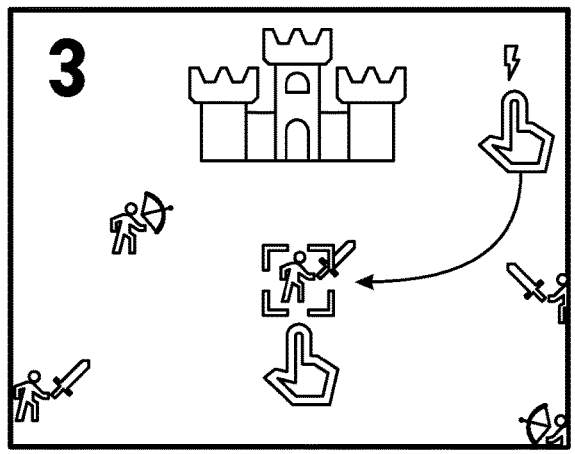
Figure 15D:
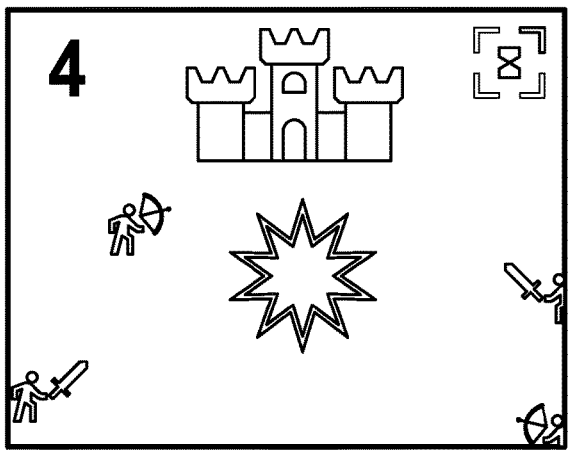

An example of a meta-game is a tower defense game. FIGS. 15A through 15D are screen shots of an example of a tower defense game. In FIG. 15A, a plurality of enemy units approach a castle of the user. In FIG. 15B, the plurality of enemy units attempt to damage the castle of the user. In FIG. 15C, the user presses on an enemy unit to initiate a defensive action against the selected enemy unit. The user plays one or more boost games to determine the effectiveness of the defensive action. In some implementations, the user needs to complete one or more boost games to perform the defensive action. For example, the defensive action may only be successful if the user successfully completes one or more boost games. Alternatively, or in addition, the odds of a successful defensive action are determined based on the user's performance while playing one or more boost games. For example, the odds of a successful defensive action may increase in response to the user successfully completing a boost game faster. Alternatively, or in addition, the user may spend points to increase the odds of a successful defensive action. Upon completion of a successful defensive action, the selected enemy unit may be destroyed, as illustrated in FIG. 15D.

In some implementations, a user is able to spend points (or other rewards) in the meta-game, for example, as described above. Alternatively, or in addition, a user to able to spend points (or other rewards) in boost games (as part of the meta-game or separate from the meta-game). For example, the user is able to spend reward points to decrease a difficulty level of the boost game play in connection with the meta-game. In some implementations, the meta-game may include metacognitive strategies to encourage the user to bank points. For example, the tower defense game may offer the user a choice between spending points now to receive a small defensive upgrade to their castle or waiting for five more turns to spend points and receive a large defensive upgrade to their castle.

In some implementations, a user suffering from a substance use dependency such as LTOT may be prescribed a medication which is reflected as a daily or weekly target morphine milligram equivalent (MME). To provide support to the user throughout the day, the daily target MME of the user can be separated into a plurality of scheduled doses. In some implementations, the user or a healthcare professional may enter the prescribed drug name and dose schedule, or several drug types and their corresponding administration schedules, upon which the substance usage management platform determines a periodic daily MME schedule from a correlative database of drug types and their MME dose equivalents. In some implementations, the substance usage management platform described herein is configured to schedule doses such that a user meets their daily or weekly target MME, and customized to drug type and MME-correlated tablet or capsule doses. For example, the substance usage management platform may schedule four 24 MME doses of oxycodone across a day for a user with a daily target of 96 MME oxycodone. While it is ideal for a user to only take scheduled doses, in real-world situations, the user may want to take a dose sooner than scheduled. For example, the user may be experiencing breakthrough pain or a substance craving. Thus, the substance usage management platform described herein may further be configured to manage doses in order to keep the user on target.

Figure 16:
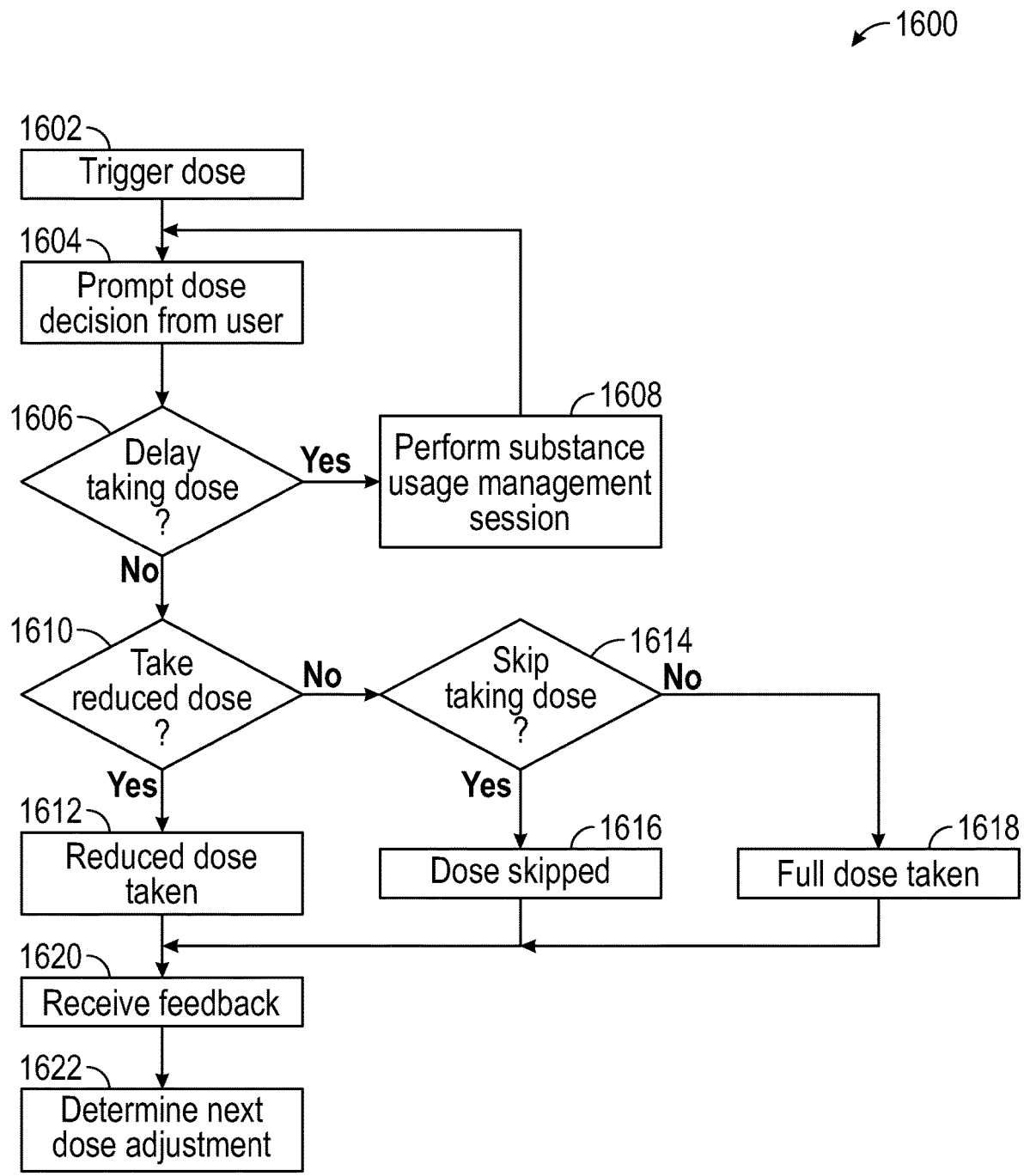
FIG. 16 is a flow diagram of an example of a method for managing a dose, in accordance with some implementations of the present disclosure.

FIG. 16 is a flow diagram of an example of a method 1600 for managing a dose. The method 1600 is performed by processing logic that may include hardware (circuitry, dedicated logic, etc.), software (such as is run on a general-purpose computer system, a dedicated machine, or a computing device of any kind (for example, IoT node, wearable, smartphone, mobile device, etc.)), or a combination of both. The method 1600 and/or each of its individual functions (including "methods," as used in object-oriented programming), routines, subroutines, or operations may be performed by one or more processors of a computing device (for example, any component of FIG. 17, as will be described below).

For simplicity of explanation, the method 1600 is depicted in FIG. 16 and described as a series of operations performed by a smartphone. However, operations in accordance with the present disclosure can occur in various orders and/or concurrently, and/or with other operations not presented and described herein. For example, the operations depicted in the method 1600 in FIG. 16 may occur in combination with any other operation of any other method disclosed herein. Furthermore, not all illustrated operations may be required to implement the method 1600 in accordance with the disclosed subject matter. In addition, those skilled in the art will understand and appreciate that the method 1600 could alternatively be represented via a state diagram or event diagram as a series of interrelated states.

At block 1602, a dose is triggered. The dose may be triggered in response to a scheduled dose for a user. For example, when a user is scheduled to take a dose at 2:00 PM, the dose may be triggered at 2:00 PM or at a predetermined time before 2:00 PM, such as at 1:55 PM. The dose may also be triggered by a user-perceived substance craving. For example, a user may provide input to the smartphone indicating that the user is suffering a substance craving. The dose may also be triggered by a direct user request. For example, a user may provide input to the smartphone requesting a dose because the user is experiencing a high amount of pain. A user-requested dose is sometimes referred to a pro re nata (PRN) dose or a breakthrough dose. The dose may also be triggered in response to detecting a pain event via biometric feedback. For example, the smartphone may determine that a user is likely experiencing a pain event based on biometric feedback about the user's state such as pupillary size, skin temperature, heart rate, heart rate variability, photoplethysmographic SpO2, galvanic skin response (or electrodermal activity), and movement (as detected, for example, by an inertial measurement unit or electromyography sensor). The dose may alternatively be triggered by a smartphone profile corresponding to a predicted drug craving (for example, a profile based on factor model data including biometric correlation to prior craving events, biometric data correlated to circadian cycle point, smartphone metadata including time of day and current location, proximity to measurable environmental craving or pain triggers, or aggregated craving profile data from other users indicating elevated likelihood of a craving event in the next several minutes to one hour).

Responsive to the dose being triggered, a dose decision is prompted from the user, at block 1604. The dose decision represents an action that the user wants to take. For example, the smartphone may display a prompt asking whether the user wants to delay taking the dose, take a reduced dose, skip the dose, or take the full dose. In some implementations, the prompt for the dose decision may include a recommendation to the user. For example, the prompt for the dose decision may recommend that the user take a reduced dose or attempt to delay taking the dose. In some implementations, the prompt for the dose decision may include cascading recommendations. For example, the prompt for the dose decision may initially recommend that the user attempt to take a reduced dose, and in response to a rejection from the user, subsequently recommend that the user delay taking the dose. In some implementations, when the dose is triggered by biometric feedback indicating that the user may be experiencing a pain event or a craving event, the prompt for the dose decision may request the user to indicate whether the user is currently experiencing pain or a craving. In response to a positive acknowledgement from the user, the smartphone may provide a recommendation for the user. For example, when the user acknowledges that the user is experiencing pain, the smartphone may display a recommendation that the user take a reduced dose and engage in boost games designed to address pain perception.

Next, at block 1606, the smartphone determines whether the user wants to delay taking the dose. For example, the smartphone may determine that the user wants to delay taking the dose when the user responds to the dose decision prompt by requesting a delay in taking the dose. Further, the smartphone may determine that the user does not want to delay taking the dose when the user responds to the dose decision prompt by requesting to take a reduced dose, requesting to skip taking the dose, or requesting to take the full dose. When the user wants to delay taking the dose, a substance usage management session (such as described above in relation to FIG. 9) is performed at block 1608. After performing the substance usage management session, the method 1600 returns to block 1604 and another dose decision is prompted from the user.

Returning to block 1606, when the user does not want to delay taking the dose, the smartphone determines whether the user wants to take a reduced dose at block 1610. A reduced dose may include any size or amount that is smaller than a full dose. The smartphone may determine that the user wants to take a reduced dose when the user responds to the dose decision prompt by requesting to take a reduced dose. For example, for a dose including two tablets of a substance, the user may want to take a reduced dose of only one tablet. Reducing a dose by one tablet may be referred to as a "pill drop." Further, the smartphone may determine that the user does not want to take the reduced dose when the user responds to the dose decision prompt by requesting to skip taking the dose or requesting to take the full dose. When the user wants to take a reduced dose, a reduced dose is taken at block 1612.

Returning to block 1610, when the user does not want to take a reduced dose, the smartphone determines whether the user wants to skip taking the dose at block 1614. For example, the smartphone may determine that the user wants to skip taking the dose when the user responds to the dose decision prompt by requesting to skip taking the dose. Further, the smartphone may determine that the user wants to take the dose when the user responds to the dose decision prompt by requesting to take a reduced dose or requesting to take the full dose. When the user wants to skip taking the dose, the dose is skipped at block 1616. Alternatively, when the user does not want to skip the dose (i.e., the user wants to take the full dose), the full dose is taken at block 1618.

After the reduced dose is taken at block 1612, the dose is skipped at block 1616, or the full dose is taken at block 1618, feedback is received at block 1620. Feedback may include user feedback such as a pain level, a mood indicator, and a mobility indicator. For example, the user may be prompted to provide a user pain level indicating of how much pain the user is currently experiencing. Feedback may also include biometric information about the user such as pupillary size, skin temperature, heart rate, heart rate variability, PPG SpO2, galvanic skin response, and movement.

Next, at block 1622, a next dose adjustment is determined. The next dose adjustment may include a recommendation to the user on how to adjust the next dose. For example, the next dose adjustment may include a recommendation to delay taking the next dose by thirty minutes. The next dose adjustment may be determined based on the medication type and tablet or capsule size, and whether the user takes a reduced dose, skips taking the dose, or takes the full dose. For example, when the user skips taking the dose, the next dose adjustment may include a recommendation to take a full dose at the next scheduled dose. The next dose adjustment may also be determined based on whether and by how long the user delays taking the dose. For example, when the user delays taking the dose for fifteen minutes, the next dose adjustment may include a recommendation to delay the next dose for thirty minutes. The next dose adjustment may further be determined based on the feedback received at block 1620. For example, when the feedback indicates that the user is experiencing moderate pain, the next dose adjustment may include a recommendation to take a full dose at the next scheduled dose. In some implementations, the next dose adjustment is determined based on a target MME for the user. For example, when the user's actions during the current dose may result in exceeding a daily target MME for the user, the next dose adjustment may be determined to get the user back on track.

Figure 17:
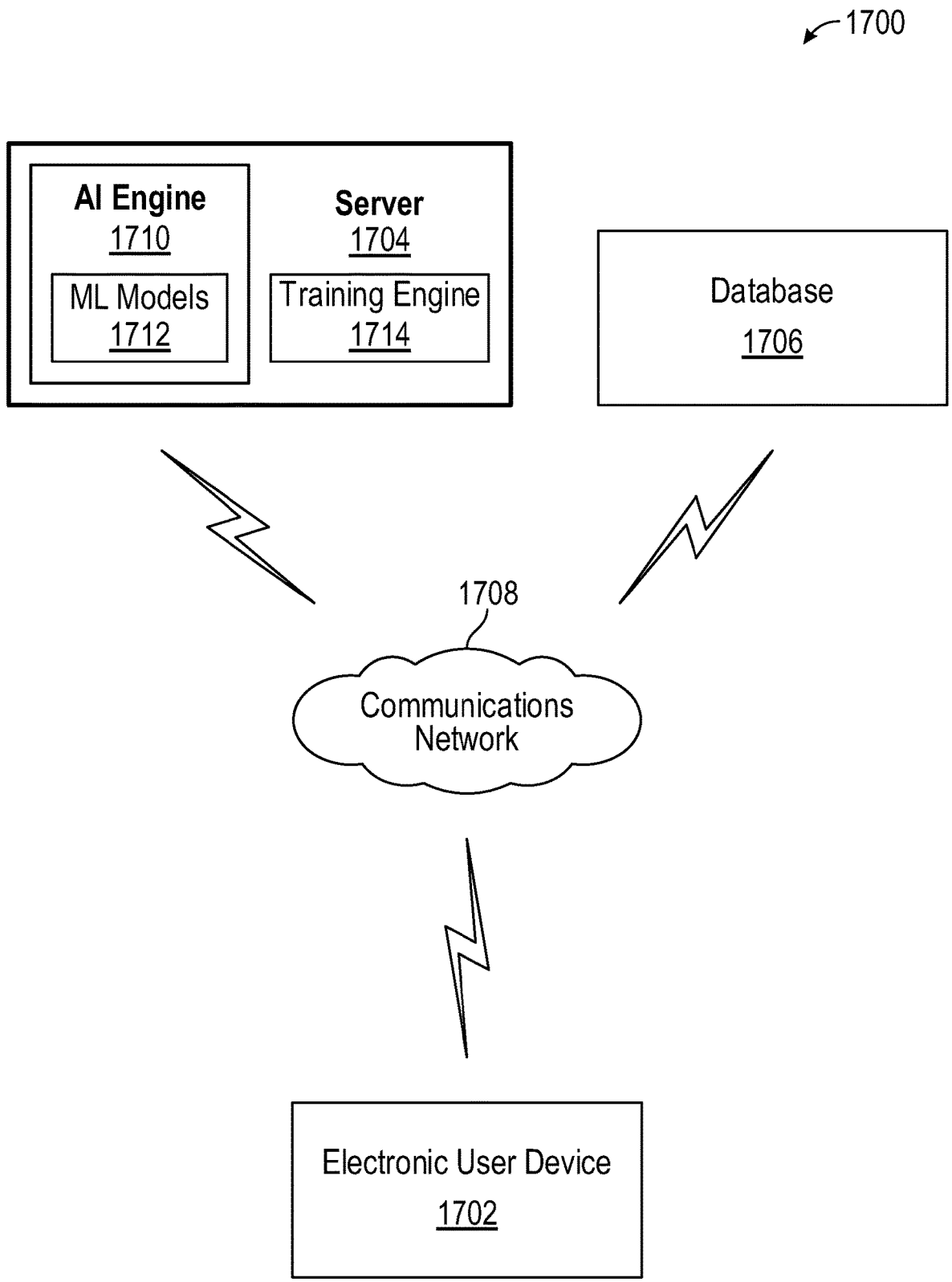
FIG. 17 is a block diagram of an example of a system for substance usage management, in accordance with some implementations of the present disclosure.

FIG. 17 is a block diagram of an example of a system 1700 for substance usage management. The system 1700 is an example of a substance usage management platform. The system 1700 illustrated in FIG. 17 includes an electronic user device 1702, a server 1704, a database 1706, and a communications network 1708. The system 1700 may include fewer, additional, or different components in different configurations than the system 1700 illustrated in FIG. 17. For example, in some implementations, the system 1700 may include multiple electronic user devices. The electronic user device 1702 may include a smartphone, a tablet, a laptop computer, a desktop computer, or a combination thereof. The communications network 1708 may be a wired network, a wireless network, or both. All or parts of the communications network 1708 may be implemented using various networks, for example, a cellular network, the Internet, a Bluetooth™ network, a wireless local area network (for example, Wi-Fi), a wireless accessory Personal Area Networks (PAN), cable, an Ethernet network, satellite, a machine-to-machine (M2M) autonomous network, and a public switched telephone network. The electronic user device 1702, the server 1704, and the database 1706 communicate with each other over the communications network 1708 using suitable wireless or wired communication protocols. In some implementations, communications with other external devices (not shown) occur over the communications network 1708.

In some implementations, the server 1704 executes an artificial intelligence (AI) engine 1710 that uses one or more machine learning models 1712 to perform at least one of the implementations disclosed herein. The server 1704 may include a training engine 1714 capable of generating the one or more machine learning models 1712. The training engine 1714 may be a rackmount server, a router computer, a personal computer, a portable digital assistant, a smartphone, a laptop computer, a tablet computer, a netbook, a desktop computer, an Internet of Things (IoT) device, any other desired computing device, or any combination of the above. The training engine 1714 may be cloud-based, a real-time software platform, or an embedded system (for example, microcode-based and/or implemented) and it may include privacy software or protocols, and/or security software or protocols.

Figure 18:
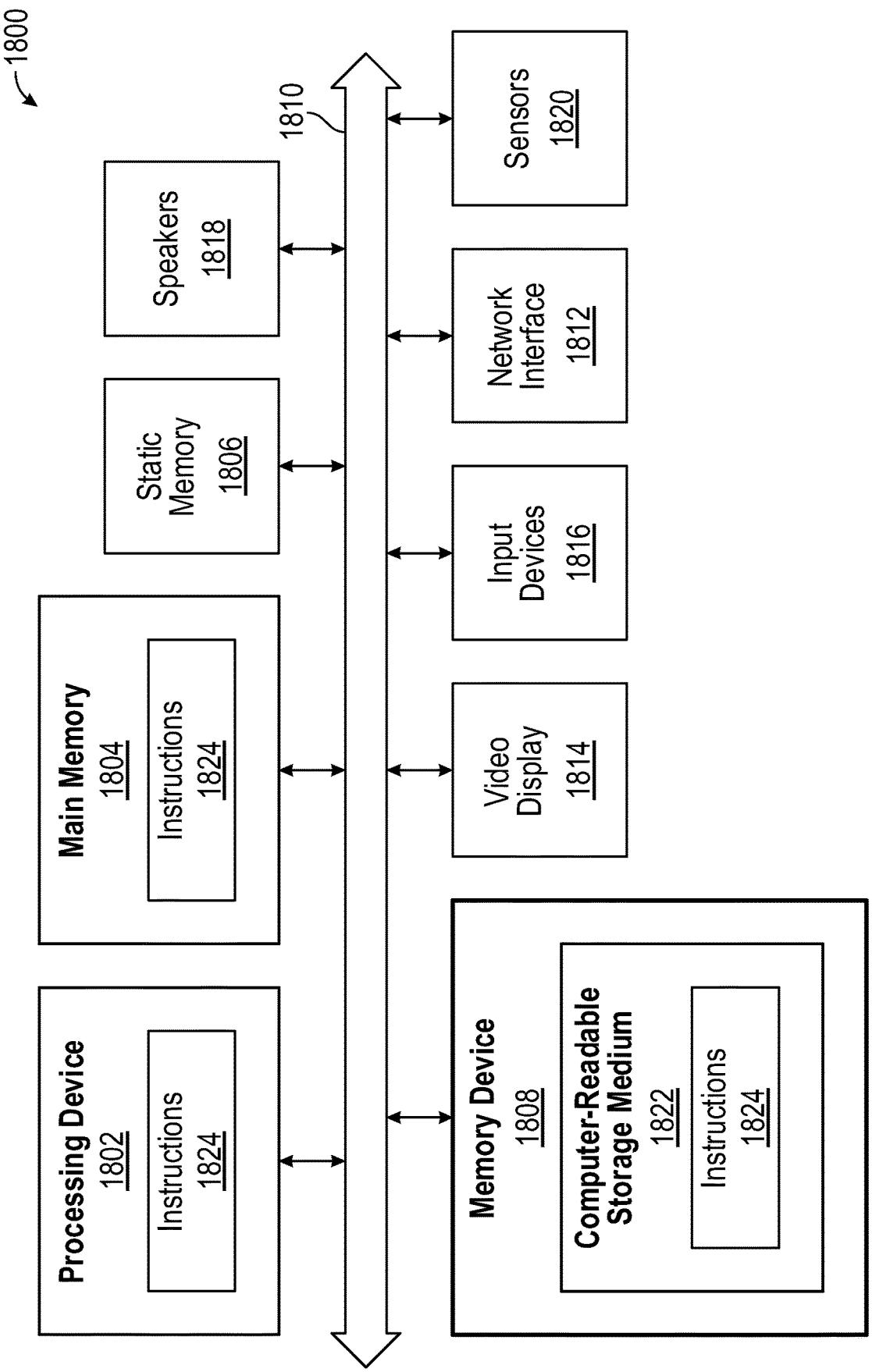
FIG. 18 is a block diagram of an example of a computer system, in accordance with some implementations of the present disclosure.

FIG. 18 is a block diagram of an example of a computer system 1800. The computer system 1800 may be connected (for example, networked) to other computer systems in a LAN, an intranet, an extranet, or the Internet, including via the cloud or a peer-to-peer network. The computer system 1800 may operate in the capacity of the electronic user device 1702, the server 1704, and/or the database 1706 of the system 1700 illustrated in FIG. 17. The computer system 1800 may be a personal computer (PC), a tablet computer, a wearable (for example, wristband), a set-top box (STB), a personal Digital Assistant (PDA), a mobile phone, a smartphone, a camera, a video camera, an Internet of Things (IoT) device, or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 1800 illustrated in FIG. 18 includes a processing device 1802, a main memory 1804 (for example, read-only memory (ROM), flash memory, solid state drives (SSDs), dynamic random access memory (DRAM) such as synchronous DRAM (SDRAM)), a static memory 1806 (for example, flash memory, solid state drives (SSDs), static random access memory (SRAM)), and a memory device 1808, which communicate with each other via a bus 1810.

The processing device 1802 represents one or more general-purpose processing devices such as a microprocessor, central processing unit, or the like. More particularly, the processing device 1802 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 1802 may also be one or more special-purpose processing devices such as an application specific integrated circuit (ASIC), a system on a chip, a field programmable gate array (FPGA), a digital signal processor (DSP), network processor, or the like. The processing device 1802 may be configured to execute instructions for performing any of the operations and steps discussed herein.

The computer system 1800 illustrated in FIG. 18 further includes a network interface 1812. The computer system 1800 also may include a video display 1814 (for example, a liquid crystal display (LCD), a light-emitting diode (LED), an organic light-emitting diode (OLED), a quantum LED, a cathode ray tube (CRT), a shadow mask CRT, an aperture grille CRT, a monochrome CRT), input devices 1816 (for example, one or more microphones, a keyboard and/or a mouse or a gaming-like control), and one or more speakers 1818 (for example, a speaker). In one illustrative example, the video display 1814 and the input devices 1816 may be combined into a single component or device (for example, an LCD touch screen). The computer system 1800 illustrated in FIG. 18 further includes one or more sensors 1820 such as temperature sensors, accelerometers, magnetic field sensors, gyroscopes, proximity sensors, pressure sensors, light sensors, GPS sensors (or other position sensors), heart rate sensors, and fingerprint sensors.

The memory device 1808 may include a computer-readable storage medium 1822 on which the instructions 1824 embodying any one or more of the methods, operations, or functions described herein is stored. The instructions 1824 may also reside, completely or at least partially, within the main memory 1804 and/or within the processing device 1802 during execution thereof by the computer system 1800. As such, the main memory 1804 and the processing device 1802 also constitute computer-readable media. The instructions 1824 may further be transmitted or received over a network via the network interface 1812.

While the computer-readable storage medium 1822 is shown in the illustrative examples to be a single medium, the term "computer-readable storage medium" should be taken to include a single medium or multiple media (for example, a centralized or distributed database, and/or associated caches and servers) that store the one or more sets of instructions. The term "computer-readable storage medium" shall also be taken to include any medium capable of storing, encoding or carrying out a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

A user may follow a treatment plan to, for example, reduce substance usage, alleviate symptoms of substance cravings, and improve user self-control. A treatment plan may be entered by the user or a healthcare professional or be system-generated, may include a daily or weekly target MME. A treatment plan may also include a dosage schedule configured to achieve a daily or weekly target MME. For example, a treatment plan may indicate that a user should take a specific dose of a substance every nine hours each day. A treatment plan may also include specific boost games. For example, a treatment plan may indicate a specific set of boost games for a user to play during a substance usage management session. Further, a treatment plan may indicate different boost games for a user to play during different situations. For example, a treatment plan may indicate a first set of boost games for a user to play during a substance craving and a second set of boost games for the user to play while delaying a scheduled dose. A treatment plan may also include specific parameters for boost games. For example, a treatment plan may indicate automatic and user-selected thresholds for key task parameters for each type of boost game. A key task parameter for a boost game may include, for example, a deviation of a delayed action from a target delay-time. A treatment plan may also include behavioral or lifestyle modification recommendations for the user in response to chronotype or circadian rhythm phase data. For example, a treatment plan may include sleep hygiene guides, food ingestion schedules, supplement administration suggestions, or a combination thereof.

Correlating a specific user's attributes and performance results with known data for a cohort of other users enables generation of treatment plans. Therefore, it may be desirable to process the attributes of a multitude of users, treatment plans performed by those users, and the results of treatment plans for those users. Accordingly, in some implementations, systems and methods, such as those described herein, use artificial intelligence and/or machine learning to generate treatment plans. For example, the machine learning models 1712 may be trained to assign users to certain cohorts based on their attributes, select treatment plans using real-time and historical data correlations involving user cohort-equivalents, and control the substance usage management platform, among other things. In some implementations, the substance usage management platform develops treatment plans which are capable of predicting an increased likelihood of an onset of a craving or elevated pain event, in for example, a minutes to hours timeframe, with this prediction data resulting in configurations of the system which modify information presented to the user, or which prompt the user to begin a substance usage management session. The one or more machine learning models 1712 may be generated by the training engine 1714 and may be implemented in computer instructions executable by one or more processing devices of the training engine 1714 and/or the server 1704. To generate the one or more machine learning models 1712, the training engine 1714 may train the one or more machine learning models 1712. The one or more machine learning models 1712 may be used by the artificial intelligence engine 1710.

To train the one or more machine learning models 1712, the training engine 1714 may use a training data set of a corpus of the attributes of the users that used the substance usage management platform to perform treatment plans, the details (for example, parameters/configurations/settings for boost games, system engagement and utilization patterns by the user, and user generated data) of the treatment plans performed by the users using the substance usage management platform, and the results of the treatment plans performed by the users. In some implementations, the training data set may include weekly calibration data (for example, from check-in sessions), utilization data for boost games (for example, the numbers of trials completed), choice-making data (for example, rewards or points accumulation or disposition choices), performance data for boost games, and threshold values for boost games (for example, automatic and user-selected thresholds). The one or more machine learning models 1712 may be trained to match patterns of attributes of a user with attributes of other users assigned to a particular cohort. The term "match" may refer to an exact match, or to correspondences, associations, relationships, approximations or other mathematical, linguistic and other non-exact matches, including, for example, a correlative match, a substantial match, a partial match, an associative match, a relational match, etc. The one or more machine learning models 1712 may be trained to receive the attributes of a user as input, to map the attributes to attributes of user assigned to a cohort, and to select a treatment plan from that cohort. The one or more machine learning models 1712 may also be trained to control, based on the treatment plan, the substance usage management platform.

Using training data that includes training inputs and corresponding target outputs, the one or more machine learning models 1712 may refer to model artifacts created by the training engine 1714. The training engine 1714 may find patterns in the training data wherein such patterns map the training input to the target output, and generate the machine learning models 1712 that capture these patterns. In some implementations, the artificial intelligence engine 1710 and/or the training engine 1714 may reside on another component depicted in FIG. 17 (for example, the electronic user device 1702 or the database 1706).

The one or more machine learning models 1712 may comprise, for example, a single level of linear or non-linear operations (for example, a support vector machine [SVM]) or parametric or nonparametric multi-level models or LASSO regression models, or the machine learning models 1712 may be a deep network, i.e., a machine learning model comprising multiple levels of non-linear operations. Examples of deep networks include neural networks, and neural networks may include generative adversarial networks, convolutional neural networks, recurrent neural networks with one or more hidden layers, and fully connected neural networks (for example, wherein each neuron may transmit its output signal to the input of the remaining neurons, as well as to itself). For example, the machine learning model may include numerous layers and/or hidden layers that use various neurons to perform calculations (for example, dot products).

Figure 19:
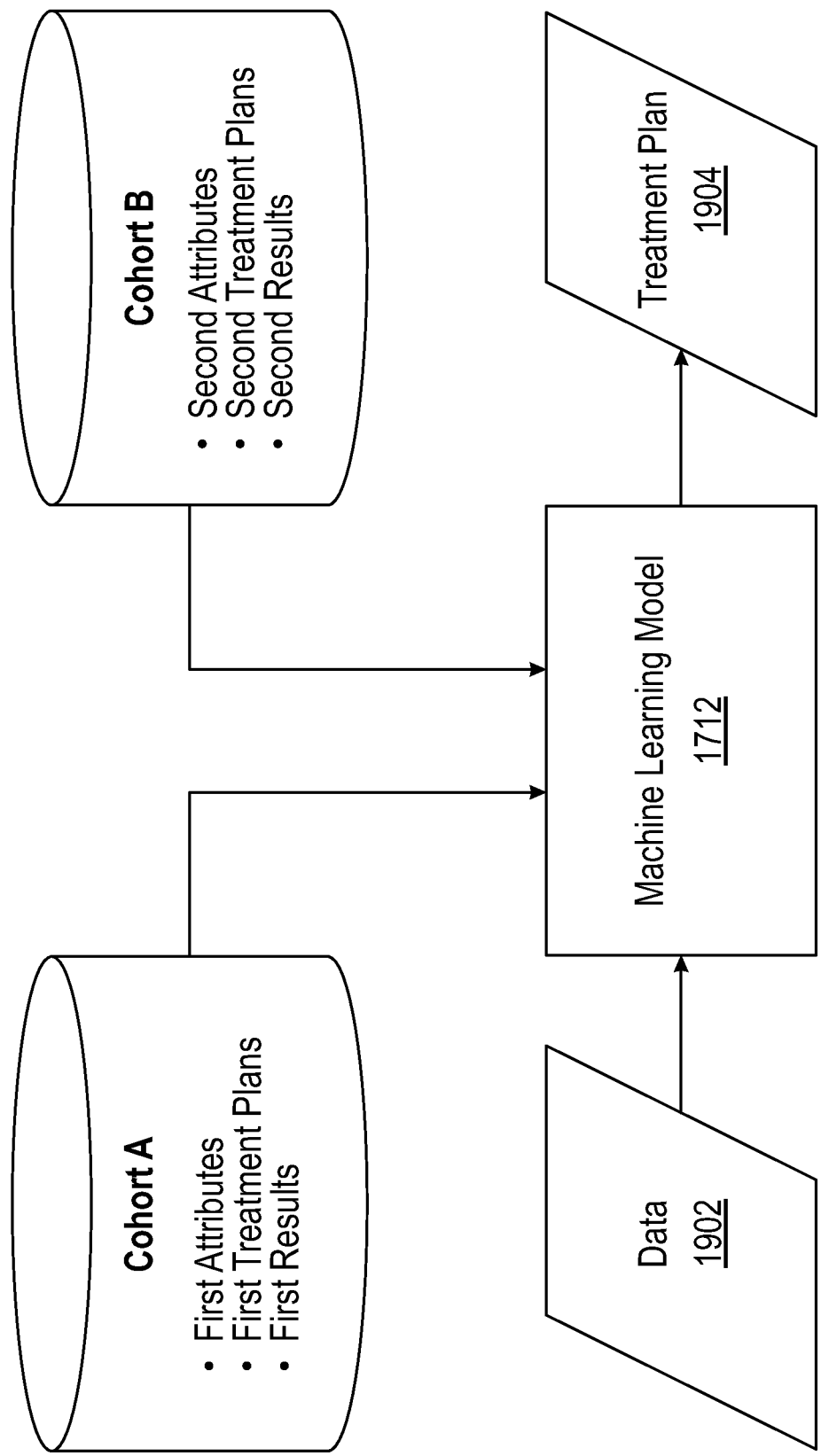
FIG. 19 is a block diagram of an example of training a machine learning model, in accordance with some implementations of the present disclosure.

FIG. 19 shows a block diagram of an example of training the machine learning model 1712 to output, based on data 1902 associated with the user, a treatment plan 1904 for the user according to the present disclosure. Data pertaining to other users of the substance usage management platform may be received by the server 1704. The data may include attributes of the other users, the details of treatment plans performed by the other users, and/or the results of performing the treatment plans (for example, an amount of pain or discomfort experienced by the user, an amount of increase or decrease in substance usage, an amount of increase or decrease in substance craving frequency or intensity, etc.). User reported qualia and information during substance cravings (for example, event, intensity, duration, and triggers) and during check-ins may be included as training data or validation data for the machine learning model 1712. Additional training data may include records of recent smartphone interaction activity such as call or text message patterns (for example, frequency, contacts, and duration or content of interactions) which preceded the substance craving event over minutes-long to days-long duration prior to the event.

As depicted in FIG. 19, the data has been assigned to different cohorts. Cohort A includes data for users having similar first attributes, first treatment plans, and first results. Cohort B includes data for users having similar second attributes, second treatment plans, and second results. For example, cohort A may include first attributes of users in their twenties, and wherein such users were prescribed opioids to recover from a broken limb; their treatment plans may include a certain treatment protocol (for example, play a specific set of boost games during a substance craving, wherein values for the properties, configurations, and/or settings of the boost games are set to X (wherein X is a numerical value) for the first two weeks and to Y (wherein Y is a numerical value) for the following week).

As further depicted in FIG. 19, cohort A and cohort B may be included in a training dataset used to train the machine learning model 1712. The machine learning model 1712 may be trained to match a pattern between one or more attributes for each cohort and to output the treatment plan 1904 that provides the result, i.e., the best match. Accordingly, when the data 1902 for a new user is input into the trained machine learning model 1712, the trained machine learning model 1712 may match the one or more attributes included in the data 1902 with one or more attributes in either cohort A or cohort B and output the appropriate treatment plan 1904. In some implementations, the machine learning model 1712 may be trained to output one or more excluded treatment plans that should not be performed by the new user.

The artificial intelligence engine 1710 may compare the expected results of a treatment plan to the actual results of the treatment plan. Results may include substance usage (for example, full doses taken, reduced doses taken, doses skipped, and doses delayed), results of check-in sessions, user performance during boost games, and biological conditions (for example, one or more vital signs of the user, a respiration rate of the user, a heartrate of the user, a temperature of the user, a blood pressure of the user, etc.). The artificial intelligence engine 1710 may determine that the treatment plan is optimal for the particular user (i.e., the user is having a desired result) if one or more parts or portions of the actual results are within an acceptable range associated with one or more corresponding parts or portions of the expected results (for example, within one or more thresholds). Conversely, the artificial intelligence engine 1710 may determine that the treatment plan is not optimal for the particular user (i.e., the user is not having a desired result) if one or more parts or portions of the actual results are outside of the range associated with one or more corresponding parts or portions of the expected results (for example, outside of the one or more thresholds). For example, the artificial intelligence engine 1710 may determine that a treatment plan is not optimal for the particular user when the actual substance usage of the user exceeds a target MME of the treatment plan by more than a threshold amount.

In some implementations, the artificial intelligence engine 1710 may determine that the treatment plan is not optimal for a particular user if one or more parts or portions of the actual results are within an acceptable range associated with one or more corresponding parts or portions of the expected results for an extended period of time. For example, when a treatment plan is successful in keeping substance usage of a user at or under a target MME of the treatment plan for several weeks, a modified treatment plan with a lower target MME may become optimal. Further, delaying the time at which a dose is taken practically translates to a dose reduction. For example, one hour of delay may translate to a one-third dose reduction. Thus, in some implementations, the artificial intelligence engine 1710 (or another component of the server 1704) may recommend a modified treatment plan with a lower target MME. For example, after the successful cumulative delay of ninety minutes during the last twenty-four hours (resulting in a decrease of half a tablet), a modified treatment plan in which the target MME is lowered by one tablet may be recommended. In some implementations, a recommendation for a modified treatment plan is sent to a healthcare professional to review and adjust as deemed appropriate before execution by the substance usage management platform. For example, a healthcare professional may determine whether to implement the modified treatment plan, make changes to the plan, or request a new modified plan for review. In some implementations, treatment plans, threshold alerts regarding plan attributes, and other plan data or user data may be viewed, modified, and approved by the healthcare professional or by a non-user administrator using a remote online portal system, or may be communicated in summary format to the healthcare profession by electronic mail or other asynchronous and secure electronic means. In some implementations, the substance usage management platform modifies treatment plans based on changes in user psychometric data or biometric information (for example, detection of alterations in acrophase parameters in last three days, compared to the last thirty days).

In some implementations, the artificial intelligence engine 1710 may interact with the electronic user device 1702 to provide treatment plan input indicating one or more modifications to the treatment plan and/or to one or more attributes of the boost games if the artificial intelligence engine 1710 determines to modify the treatment plan and/or the one or more attributes of the boost games. For example, the electronic user device 1702 may provide input indicating an increase or decrease in a difficulty setting of a boost game, an increase or decrease in an amount of time the user plays a boost game, or other suitable modification to the one or more attributes of a boost game.

In some implementations, the substance usage management platform may be configured to modify the treatment plan based on one or more modifications indicated by the treatment plan input. Alternatively, or in addition, the substance usage management platform may be configured to modify the one or more attributes of one or more boost games based on the modified treatment plan and/or the treatment plan input. For example, the treatment plan input may indicate to modify the one or more attributes of a boost game and/or the modified treatment plan may require or indicate adjustments to the boost game in order for the user to achieve the desired results of the modified treatment plan. Attributes may include game reward parameters (for example, point scoring and performance rewards systems). Attributes may also include game difficulty parameters (for example, task challenge, task complexity, and modal complexity).

Opioids and other substances such as alcohol, caffeine, and psychiatric medications, may cause circadian dysfunctions and other circadian changes. In some implementations, the substance usage management platform is configured to adjust the time and/or size of scheduled doses based on a circadian cycle of the user. For example, the substance usage management platform may adjust the time and/or size of scheduled doses to lower potential side effects of opioids such as sleep dysfunction. In some implementations, the substance usage management platform is configured to gather various biosignals about a user in order to track a circadian cycle of the user. The substance usage management platform may be configured using a combination of biosignals of the user and other types of signals data (for example, light levels, sound levels, and temperature levels of the local environment) derived from one or more devices (for example, from an environmental sensor, a wearable device, a smartphone sensor, an IoT device, or a network data resource). In some implementations, transformations of combinations of sensor data (for example, moving averages, bandpass filtering, and thresholding) and coincidence detection methods may be used to improve data quality and to configure the substance usage management platform. Various biosignals and raw or transformed sensor data may serve as inputs for the artificial intelligence engine 1710.

Figure 20:
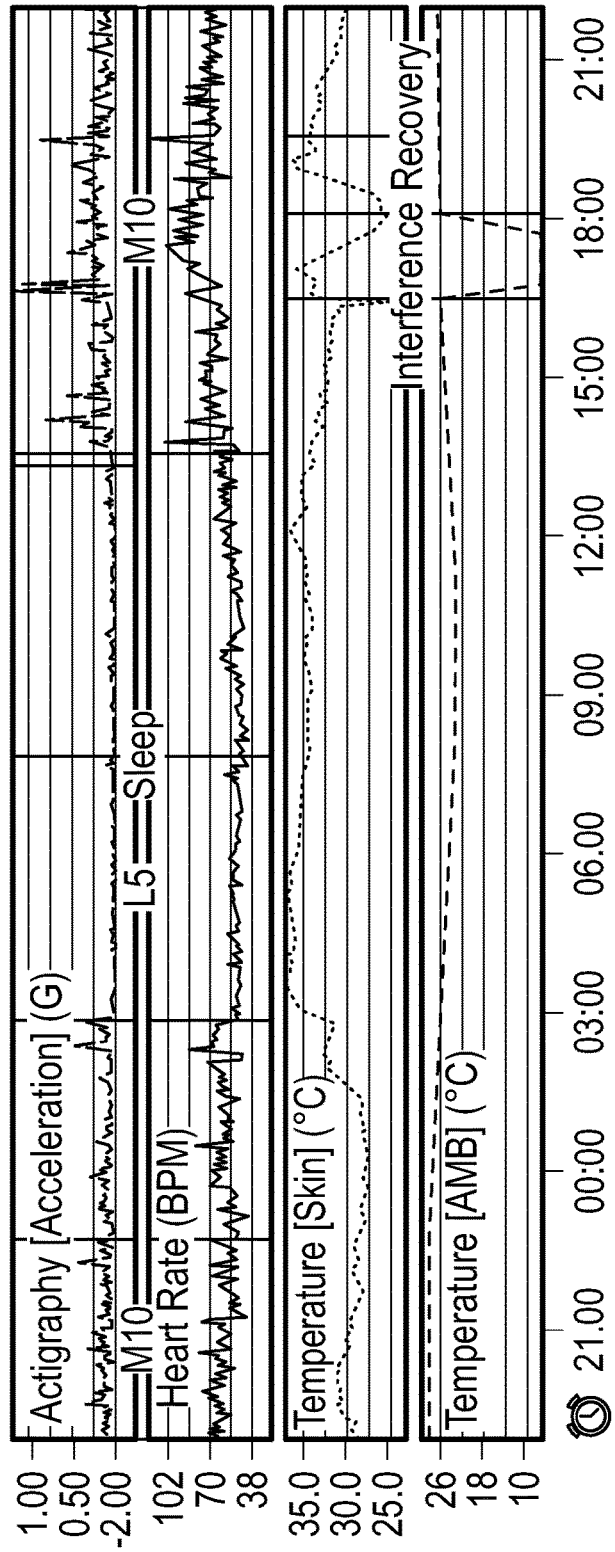
FIG. 20 are plots of examples of biosignals of a user over a twenty-four hour period, in accordance with some implementations of the present disclosure.

FIG. 20 illustrates plots of examples of various biosignals of a user (for example, heart rate, skin surface temperature, and inertial movement data as measured by a wearable device) and examples of signals relating to the environment local to the user (for example, air temperature collected from a wearable device) collected over a twenty-four hour time period. In particular, the top plot in FIG. 20 is an example of movement of the user over the twenty-four hour time period. Movement of the user may be determined by one or more acceleration sensors included, for example, in a smartphone of the user or a wearable device worn by the user. The upper middle plot in FIG. 20 is an example of a heart rate of the user over the twenty-four time hour period. The heart rate of the user may be determined by one or more heart rate sensors included, for example, in a smart watch or other fitness tracker worn by the user. The lower middle plot in FIG. 20 is an example of a skin temperature of the user over the twenty-four time hour period. The skin temperature of the user may be determined by one or more skin sensors included, for example, in a smart watch or other fitness tracker worn by the user. The bottom plot in FIG. 20 is an example of an ambient temperature over the twenty-four hour time period. Ambient temperature may be determined by one or more temperature sensors included, for example, in a smartphone of the user, a wearable device worn by the user, or a stand-alone device. The plots for temperature in FIG. 20 indicate, for example, a period of trend divergence between environmental data and skin surface data at 15:00 to 18:00 which, in some implementations, are identified (for example, by an error correction system, a noise reduction module, a data cleaning module, or by the artificial intelligence engine 1714) as potentially spurious and removed from training data sets or marked in training data sets.

Figure 21:
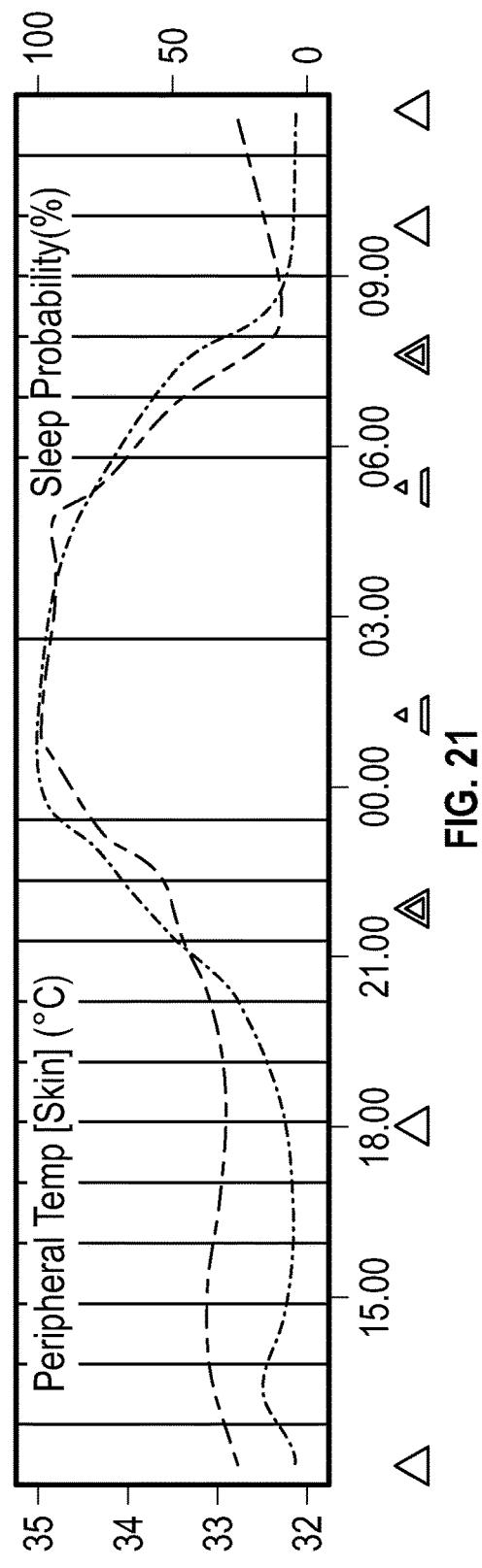
FIG. 21 are plots of examples of biosignals of a skin temperature of a user and a probability that the user is sleeping over a twenty-four hour period, in accordance with some implementations of the present disclosure.

The substance usage management platform may determine a plurality of chronobiological parameters based on the biosignals, or based on a combination of biosignals and other user data, such as user-provided or system-recorded data, for example, age, gender, body mass index, medical conditions including diagnosed sleep disorders, lifestyle habits including caffeine ingestion and exercise practices, sleep companionship habits, frequency and duration of daylight exposure and blue light exposure over a twenty-four or forty-eight hour time period, current medication list, and user-perceived alertness or sleepiness at various times in a twenty-four or forty-eight hour time period. Chronological parameters may include single-factor or composite measures which are either cross-sectional or time-varying, and may include actigraphic patterns, sleep and wake architecture measures, and chronotype scores (for example, sleep probability at cycle point, total sleep time (TST), sleep period (SLP), latency to persistent sleep (LPS), sleep episodes (SEP), SE (sleep efficiency), time in bed (TIB), wake after sleep onset (WASO), sleep onset latency (SL or SOL), duration of the sleep episode (DSE), time attempting to sleep after final awakening (TASAFA), wake minutes during TIB (WMIN), long wake episode (LWEP), activity index (ACTX), sleep fragmentation index (SFX), activity counts for the most active 10 hour time period (M10), activity counts for the most active 5 hour time period (l5), interdaily stability (IS), intradaily variability (IV), M10/L5 ratio, IS/IV ratio, circadian function index (CFI), and chronotype by LPS and TIB). The substance usage management platform may determine the circadian cycle trend and real-time circadian rhythm phase of the user based on the chronobiological parameters. For example, FIG. 21 illustrates plots of examples of a skin surface temperature of a user who is taking prescribed opioids in an LTOT regimen and a calculated probability that the user is sleeping at any given time over a representative twenty-four hour time period (sleep probability at cycle point). The filled triangles in FIG. 21 represent events of opioid usage from, for example, scheduled drug doses. The unfilled triangles in FIG. 21 represents events at which the substance usage management platform determines that user pain is lower than a baseline (for example, based on biosignals data or historical user pain reports for that time of day, or based on user responses to prompts indicating lower than normal pain intensity or other qualia). The unfilled triangles in FIG. 21 may further represent points of synchrony or divergence data. In some configurations, points of synchrony or divergence, raw or transformed biosignals data, or transformed combinations of biosgnals data and environmental data, are all examples of chronological parameters which may indicate, for example, sleep-cycle effects which may be used as training data or model inputs for the artificial intelligence engine 1710. The broken triangles in FIG. 21 represent events when the skin temperature of the user is more volatile than compared to a recent trend (for example, compared to a moving average of the current circadian cycle temperature, or in comparison to a moving average of temperature at the same point in a previous circadian cycle, or as a comparison to the average temperature from the same clock time in previous days).

Changes in skin temperature and movement compared to trends may be used to predict possible periods for which the substance usage management platform can make behavioral recommendations or offer feedback (for example, sleep hygiene recommendations, to the user). Changes in one or more various biosignals may be used to predict a possible time when the user is more or less receptive to a dose change or delay recommendation by the substance usage management platform and may be used to configure or modify a treatment plan. Changes in one or more various biosignals, and changes in relative synchrony between and among various biosignals may be used, for example, to predict a time at which the user may be more or less sensitive to opioids, to confirm that a substance dose has been taken by the user, or to indicate a likely dose if the user fails to report the dose to via the user interface.

In some implementations, the substance usage management platform may be configured to include biosignals data, in isolation or in combination with an environmental motion sensor (for example, a LIDAR sensor or infrared sensor) or a microphone or a camera device, any of which may be used to assess relative motion of the user after the user-indicated ingestion of an opioid dose. In some implementations, for a defined period of, for example, one hour after an anticipated dose of an opioid, the substance usage management platform determines a possible overdose event by detecting any occurrences of decreased heart rate, respiratory depression, lack of body movement, paucity of sound upon passive monitoring, and lack of responsiveness by the user after presentation of a visual or haptic cue on the smartphone. In some implementations, a healthcare provider may access this information in real-time and communicate with the user. A deviation of biosignals or environmental sensor data from trends, thresholds, or treatment plan ranges may indicate an elevated risk event which may trigger an electronic telephonic alert or smartphone-based alert to a healthcare professional, other user-designated individual, or to emergency responders for purposes of rescue.

The applications for the substance usage management platform may include, with condition-specific modifications of the platform, medical conditions distinct from substance dependency, which nevertheless incorporate maladaptation in impulse control and perception or choice-making processes, including bipolar disorder, compulsive gambling disorder, attention deficient disorder, attention deficit hyperactivity disorder, and post-traumatic stress disorder.

The methods described herein may be performed by processing logic that may include hardware (circuitry, dedicated logic, etc.), software (such as is run on a general-purpose computer system, a dedicated machine, or a computing device of any kind (for example, IoT node, wearable, smartphone, mobile device, etc.)), or a combination of both. The methods described herein and/or each of their individual functions (including "methods," as used in object-oriented programming), routines, subroutines, or operations may be performed by one or more processors of a computing device (for example, any component of FIG. 17, such as the server 1704). In certain implementations, the methods described herein may be performed by a single processing thread. Alternatively, the methods described herein may be performed by two or more processing threads, wherein each thread implements one or more individual functions, routines, subroutines, or operations of the methods described herein.

Individuals who experience neurotrauma (in the form, for example, of concussive injury, blunt-force injury, open head wound, clinical or subclinical traumatic brain injury (TBI), or anoxic brain injury) or chronic traumatic stress may develop maladaptive changes in memory (for example, working, long-term, or procedural), attention, information processing, motor control, decision-making, and related executive functions. Such cognitive changes may manifest as self-control impairment (sometimes referred to as "impulsivity"); observable behaviorally as, for example, suboptimal or harmful decision-making, social inappropriateness, motoric impulsivity, and impaired learning. The substance usage management platform described herein may also be used to manage users with neurotrauma (for example, concussions), stroke (for example, hemorrhagic or ischemic), and trauma-related disorders (for example, post-traumatic stress disorder (PTSD) and anxiety disorder). Decision-making reflects selected cognitive functions such as timing, attention, inhibitory control, delay tolerance, and working memory. Motoric behavior involves specific response-inhibition and circuits with some degree of overlap observed between underlying processes and their corresponding behavioral deficits, and the degree of severity and degree of recovery for any given type of neurotrauma. For example, a moderate acute closed-head TBI (for example, subclinical concussion) may exhibit as deficits in at least one of process related to decision-making, selective attention, and motoric control. In some implementations, the self-control training is combined with neurostimulation to increase the effect of treatments to improve cognitive deficits. For example, a self-control impairment management session may combine neurostimulation before and/or while a user plays one or more boost games. In some implementations, a self-control impairment management session includes at least one self-control training (SCT) boost game. SCT boost games include one or more stage two boost games, one or more stage three boost games, or a combination thereof. For example, SCT boost games may target the cognitive processes of working memory, procedural memory, ecological assessment, cognitive flexibility, choice-making, time perception, timing accuracy, inhibitory control, delay tolerance, or a combination thereof. In some implementations, for users with neurotrauma, stroke, and/or trauma-associated disorders, in addition to the cognitive processes listed above, the SCT boost games may target the cognitive processes of long-term recall (for example, hourly, daily, or weekly intervals), experiential visuospatial navigation, episodic future thinking, grounding, or a combination thereof.

Figure 22:
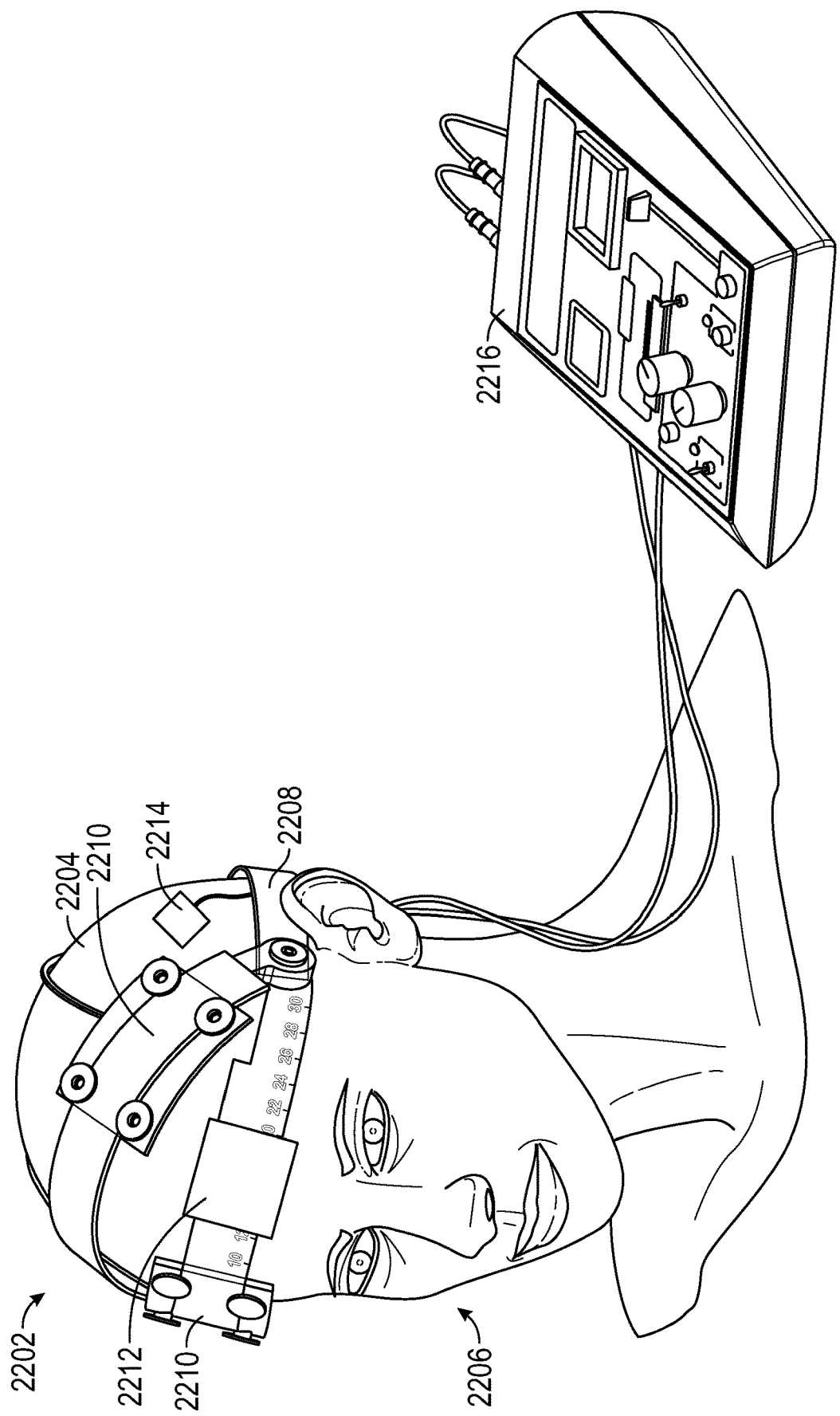
FIG. 22 is a diagram of an example of a neurostimulation device with direct current stimulation, in accordance with some implementations of the present disclosure.

FIG. 22 is a diagram an example of a neurostimulation device 2202. The neurostimulation device 2202 is configured to be worn on a head 2204 of a subject 2206 (an example of a "user"). In some implementations, the neurostimulation device may configured in a hand-held factor. The neurostimulation device 2202 illustrated in FIG. 22 includes an adjustable headband 2208, a plurality of electrodes 2210, an inertial measurement unit (IMU) 2212, a temperature sensor 2214, and a controller 2216. The neurostimulation device 2202 may include fewer components, additional components, or different components in different configurations than the neurostimulation device 2202 illustrated in FIG. 22. For example, instead of the adjustable headband 2208, the neurostimulation device 2202 may include a soft crap, a rigid headset, or an articulated band apparatus. Alternatively, or in addition, the controller 2216 may be integrated into the adjustable headband 2208.

The neurostimulation device 2202 illustrated in FIG. 22 is configured to apply direct current (DC) stimulation through the plurality of electrodes 2210 (for example, anodal or cathodal transcranial direct current stimulation (tDCS)). tDCS is a low-risk form of neuromodulation that exposes the surface of a scalp to a constant, direct current, affecting cortical regions of the brain on a regionally-localized basis, by way of non-invasive electrodes. The neurostimulation device 2202 may be configured such that use at-home or at the workplace, by an individual may be readily and safely achieved without specialized training or third-party assistance.

In some implementations, the neurostimulation device 2202 may detect when the user falls asleep. The inertial measurement unit 2212 may include one or more sensors that capture sensor data indicating movement of the user (for example, accelerometers, gyroscopes, magnetometers, etc.). Upon detecting the user has entered sleep while neurostimulation is being applied, the electronic user device 1702 (or the controller 2216) may generate an alert to wake the user. In some implementations, the inertial measurement unit 2212 is coupled to the controller 2216 via a wired connection. Alternatively, or in addition, the inertial measurement unit 2212 is coupled to the electronic user device 1702 via a wireless connection.

In some implementations, the neurostimulation device 2202 may include a light source and/or an audio speaker unit (not shown), which may serve as an alarm to remove the neurostimulation device 2202 after a period of operation.

In some implementations, the neurostimulation device 2202 may limit local heating effects and maintain safe electromagnetic radiation (EM) radiation delivery to the head 2204 of the user (for example, within a specific absorption rate (SAR) radiation dose level). The temperature sensor 2214 may include one or more sensors that capture sensor data indicating a scalp surface temperature of the user (for example, an infrared sensor or a thermocouple unit). Upon detecting the scalp surface temperature of the user is greater than a threshold, the electronic user device 1702 (or the controller 2216) may generate an alert to inform the user. Generating such alerts may prevent or reduce incidences of skin lesions that may occur in relation to local heating by the neurostimulation. In some implementations, the temperature sensor 2214 is coupled to the controller 2216 via a wired connection. Alternatively, or in addition, the temperature sensor 2214 is coupled to the electronic user device 1702 via a wireless connection.

The controller 2216 is communicable coupled to the electronic user device 1702 via a wireless connection, a wired connection, or both. The electronic user device 1702 may be configured to send and receive data from the neurostimulation device 2202 (for example, activation period timestamps, impedance, etc.) in a process of device synchronization. Alternatively, or in addition, the electronic user device 1702 may prompt the user to input data confirming that operation of the neurostimulation device 2202 has been completed for the prescribed session period. The electronic user device 1702 may select parameters for system-selected operation of the neurostimulation device 2202 (for example, current, frequency, intensity, and duration of continuous or phasic stimulation). The electronic user device 1702 may also provide calibration settings (for example, impedance measurements and position confirmation) for the neurostimulation device 2202.

Figure 23C:
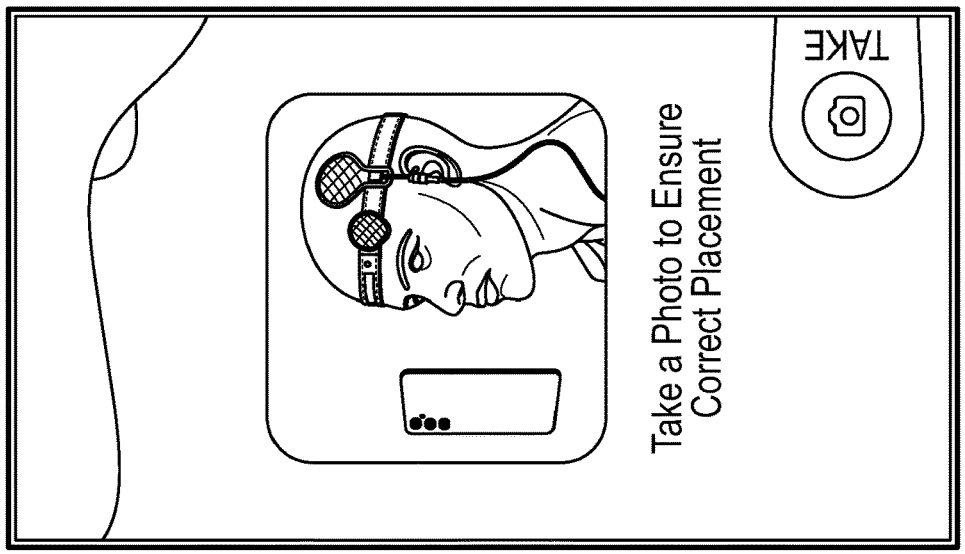
FIG. 23C is a screen shot of an example of a graphical user interface prompting a user to take a photo of a neurostimulation device to ensure correct placement, in accordance with some implementations on the present disclosure.
Figure 23B:
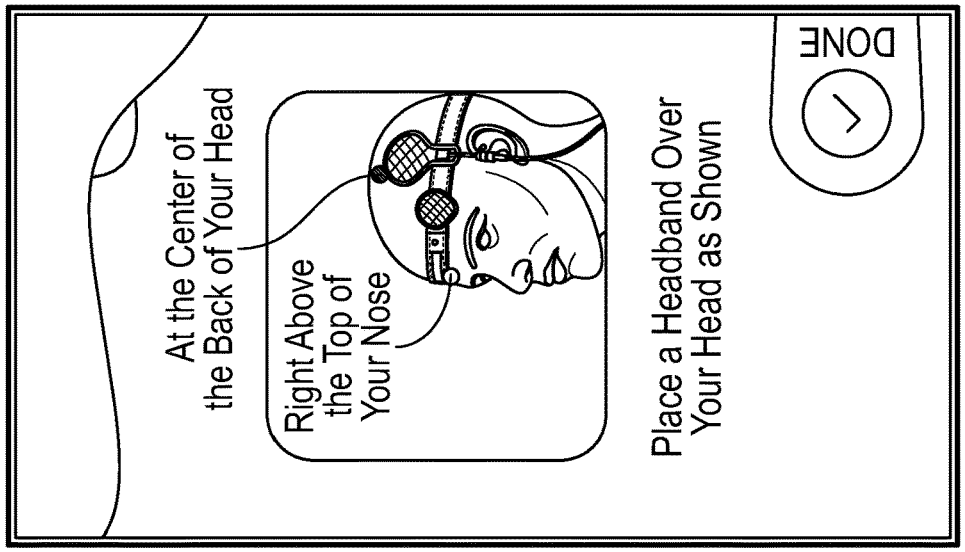
FIG. 23B is a screen shot of an example of a graphical user interface of guidance to a user on how to position a neurostimulation device on the user's head, in accordance with some implementations on the present disclosure.
Figure 23A:
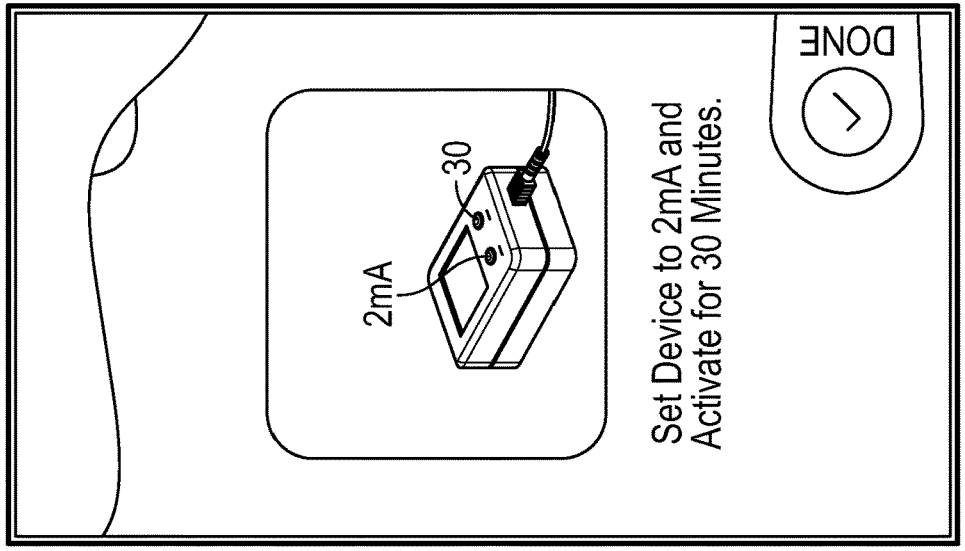
FIG. 23A is a screen shot of an example of a graphical user interface of guidance to a user for setting stimulation parameters on a neurostimulation device, in accordance with some implementations of the present disclosure.

When active, the neurostimulation device 2202 provides transcranial stimulation to the user according to a plurality of operating parameters (for example, frequency, intensity, and duration). In some implementations, the electronic user device 1702 activates the neurostimulation device 2202 by sending commands to the controller 2216. For example, the electronic user device 1702 may send commands to the controller 2216 that cause the neurostimulation device 2202 to provide transcranial stimulation with specific operating parameters. In other implementations, the electronic user device 1702 activates the neurostimulation device 2202 by displaying a graphical user interface including stimulation guidance instructions for the user. For example, FIG. 23A is a screen shot of a graphical user interface prompting the user to set the controller 2216 to 2 milliamps and activate for 30 minutes. The user may adjust the settings of the neurostimulation device 2202 with the controller 2216 based on the stimulation guidance instructions. Afterward, the user may confirm that settings of the neurostimulation device 2202 have been manually adjusted.

The neurostimulation device 2202 may include a plurality of externalized (for example, visible and discernable-to-touch) fiducial markers with a unique color and shape. Each marker may allow the user to confirm correct orientation of the neurostimulation device 2202 on the head 2204 (for example, with respect to a position relating to the nasion, the scalp occiput, a lateralized preauricular sulcus, a lateralized temporal fossa, or the scalp crown). Alternatively, or in addition, the electronic user device 1702 may display a graphical user interface that includes guidance for the user on how to place the neurostimulation device 2202 on the head 2204 of the user. For example, FIG. 23B is a screen shot of a graphical user interface including guidance for the user on how to place the neurostimulation device 2202 on the head 2204 of the user. In some implementations, the electronic user device 1702 may prompt the user to take a "selfie" photo or video. For example, FIG. 23C is a screen shot of a graphical user interface prompting the user to take a photo of the neurostimulation device 2202 to ensure correct placement. The electronic user device 1702 (or the server 1704) may confirm correct placement of the neurostimulation device 2202 upon the head 2204 based on, for example, fiducial landmark facial recognition feature extraction and photogrammetry, in comparison to a reference fiducial marker library. For example, the electronic user device 1702 (or the server 1704) may confirm placement based on facial landmarks within a specified two-dimensional planar tolerance (for example, 1 centimeter x-axis and 0.5 centimeter y-axis), in comparison to a user-specific reference image or a reference marker library. In some implementations, the electronic user device 1702 issues a position confirmation notice if the placement is within tolerance limits; and otherwise instructs the user to reposition the neurostimulation device 2202 while showing the user a marked version of the "selfie" image indicating recommended repositioning directions in the x-axis and the y-axis.

For substance use disorders, neurostimulation may be activated due to a user perception of a craving or due to a scheduled drug dose. For neurotrauma, stroke, and trauma-related disorders, neurostimulation may be activated by a scheduled prompt (as specified in a treatment plan), a random prompt (as specified in a treatment plan), electively by the user, electively by a caregiver, or a combination thereof. The need for neurostimulation may be determined based on user-perceived triggers, signs observed by caregivers, or both. For example, neurostimulation may be activated in response to a distress event. Perception of a "distress event" may include a perceived symptom of anxiety, affect shift, memory loss, confusion, or combination thereof. In some implementations, the electronic user device 1702 may be used to capture data indicating signs of disorientation, aphasia, or apraxia. For example, sentiment analysis of call audio or text messages, voice stress analysis, or other affect analysis of photographic or video data may be collected from the user.

In some implementations, the neurostimulation device 2202 may operate in a concurrent mode in which transcranial stimulation is provided to the user while the user plays boost games. Alternatively, or in addition, the neurostimulation device 2202 may operate in a priming mode in which transcranial stimulation is provided to the user before the user plays boost games. For example, in priming mode, the neurostimulation device 2202 may provide transcranial stimulation to the user for a period of thirty minutes and then stop before the user plays boost games. Alternatively, or in addition, the neurostimulation device 2202 may operate in a periodic mode in which transcranial stimulation is provided as a sequence of stimulation sessions before the user plays boost games and at the same time as the user plays boost games, up to the safety limit maximum of total stimulation.

In some implementations, before providing transcranial stimulation, the neurostimulation device 2202 performs an impedance check. For example, the neurostimulation device 2202 may determine an impedance level of the plurality of electrodes 2210 and compare the determined impedance level to a threshold (for example, a threshold of 13 Ohms). When the determined impedance level is greater than or equal to the threshold, the electronic user device 1702 may instruct the user to adjust the neurostimulation device 2202.

After a self-control impairment management session is complete, the user may be prompted to answer a series of questions relating to symptoms or signs of the condition, and a self-assessment Exit Safety Questionnaire relating to any device effects encountered by the user, such as headache or local scalp heating. User report queries may include any unusual audiovisual sensations encountered during the self-control impairment management session.

In some implementations, the system may operate in a diagnostic configuration in which boost sessions are triggered and activated on a continuous basis (for example, every three days) for purposes of identifying cognitive performance changes in boost game task completion. The user may be an individual at risk for a condition of interest. For example, the user may be a first responder, a military active duty person, or a civilian (for example, construction worker or a factory worker) at risk for neurotrauma or PTSD. As a further example, the user may have a medical history which places the user at elevated relative risk for a subclinical stroke (for example, tobacco smoking, dyslipidemia, or atrial fibrillation). In the diagnostic configuration, the minimal configuration may include the use of the software application only. A profile of the user's performance in completing boost games may be generated with and without the neurostimulation device 2202. User data may be stored (for example, in database 1706) and presented to the user and/or a healthcare professional. The system may prompt for further clinical assessment if the user data indicates sufficient deviation from normal-range profile scores to indicate injury.

In some implementations, the system may operate in a therapeutic configuration in which the neurostimulation device 2202 is used in addition to playing boost games (for example, in a self-control impairment management session). Self-control impairment management sessions may be activated based on craving events in the case of SUD and LTOT, or upon other events in the case of non-addiction related diagnoses. User data is stored (for example, in database 1706) and presented to the user and/or a healthcare professional for treatment planning.

In some implementations, the server 1704 may combine performance measures relating to boost game engagement with parameters of the neurostimulation device 2202 to define a grouping of data (for example, a score aggregation).

In some implementations, user data (for example, boost game performance, stimulation configurations, and check-in data) may be applied to an analysis pipeline to generate optimal stimulation parameters (for example, duration, regime, and pattern) and stimulation mode. User data may be incorporated into a treatment plan for the user, as generated by the artificial intelligence engine 1710 or a healthcare professional.

In some implementations, the artificial intelligence engine 1710 compares initial (baseline) and historical boost game performance data (for example, the last three sessions or the last three weeks) and check-in performance data (for example, stratification of session data collected with or without the neurostimulation device 2202) to generate a diagnosis estimate. A diagnosis estimate is a score derived from user profile data in comparison to predetermined benchmark data or to a distributional analysis of historical user-data (for example, reported as a percentile rank of performance) with scores indicating the risk of disease and disease severity. Disease diagnosis estimates and risk scores provided by the artificial intelligence engine 1710 may be condition-specific and may refer to a mild, moderate, or severe severity grading.

In the therapeutic configuration, the system may deliver periodic calibration tests to the user (for example, check-in tests including the use of the neurostimulation device 2202 in a specified stimulation mode) to determine whether the neurostimulation device 2202 is modulating user performance compared to a baseline non-stimulation performance profile. In the case that improvement is not recorded, the treatment plan may be adjusted by the artificial intelligence engine 1710 to switch the stimulation mode or to remove the neurostimulation device 2202 from the treatment plan for a specified period of time. In some implementations, adjusting one or more operating parameters of the transcranial stimulation includes removing transcranial stimulation from all or a part of a session. For example, the user may be instructed to play boost games without transcranial stimulation for a specified period of time.

In some implementations, the system determines measurements of one or more deficits in self-control related processes for a user compared to a baseline reading or a reference reading (for example, as measured by boost games and check-ins). These measurements (for example, condition grading and severity scoring) may be used in diagnosing and monitoring recovery of the user from a neurotrauma. For example, these measurements may be used to adjust a treatment plan for the user and/or for other users.

In some implementations, in addition to providing tDCS, the neurostimulation device 2202 may also provide vagal nerve stimulation. There is one vagus nerve on each side of the human body. The vagus nerve runs from the lower part of the brain through the neck to the chest and stomach. When the vagus nerve is stimulated, electrical impulses travel to areas of the brain. Pairing tDCS and vagal nerve stimulation can be used, for example, for management of LTOT for chronic pain.

In some implementations, imaging is performed immediately after completion of a session with tDCS. For example, an imaging modality (for example, an electroencephalogram (EEG) device or a functional near-infrared (fNIR) device) may capture changes in brain region activation patterns subsequent to a session. The captured changes may be used, for example, in the adaptive pipeline, treatment plan generation, or both. In some implementations, imaging data is added for a user at periodic intervals (for example, at one month, three months, and six months from initiation of use). The imaging data may be decomposed (using, for example, feature analysis, inverse modeling, and baseline correlations) to derive relative activity features for cortical and subcortical brain regions targeted for SCT training effects. After processing, the data may be added to a user treatment plan and adaptation profile, to customize a treatment plan based on relative activation of circuits compared to target activation goals.

Figure 24:
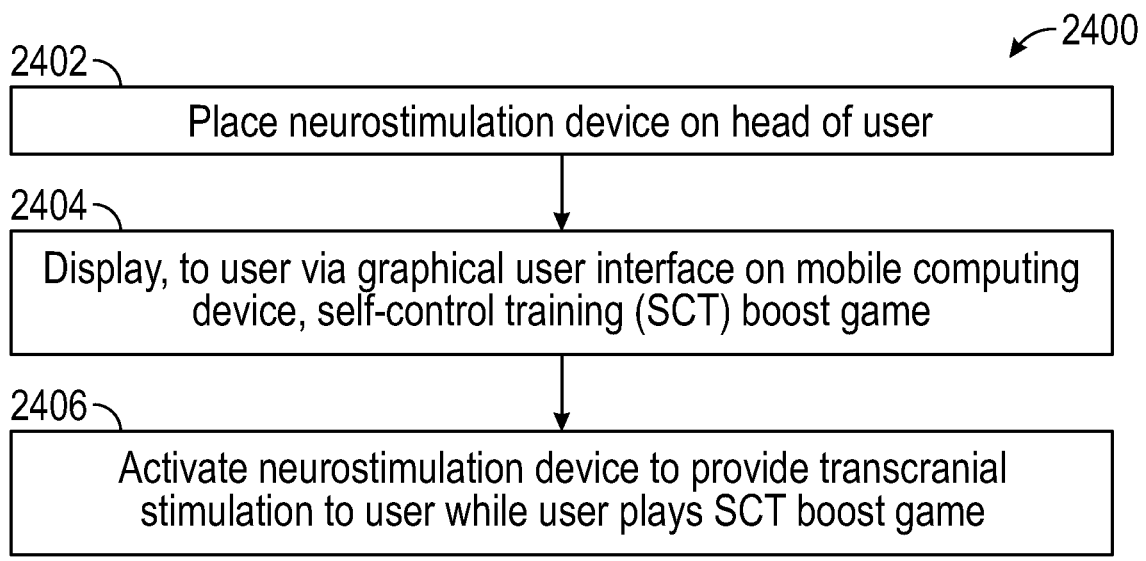
FIG. 24 is a flow diagram of an example of a method for managing self-control impairment, in accordance with some implementations of the present disclosure.

FIG. 24 is a flow diagram of an example of a method 2400 for managing self-control impairment. The method 2400 is performed by processing logic that may include hardware (circuitry, dedicated logic, etc.), software (such as is run on a general-purpose computer system, a dedicated machine, or a computing device of any kind (for example, IoT node, wearable, smartphone, mobile device, etc.)), or a combination of both. The method 2400 and/or each of its individual functions (including "methods," as used in object-oriented programming), routines, subroutines, or operations may be performed by one or more processors of a computing device (for example, any component of FIG. 17 or 22).

For simplicity of explanation, the method 2400 is depicted in FIG. 24 and described as a series of operations performed mostly by a smartphone. However, operations in accordance with the present disclosure can occur in various orders and/or concurrently, and/or with other operations not presented and described herein. For example, the operations depicted in the method 2400 in FIG. 24 may occur in combination with any other operation of any method disclosed herein. Furthermore, not all illustrated operations may be required to implement the method 2400 in accordance with the disclosed subject matter. In addition, those skilled in the art will understand and appreciate that the method 2400 could alternatively be represented via a state diagram or event diagram as a series of interrelated states.

At block 2402, the neurostimulation device 2202 is placed on a head of a user. At block 2404, a SCT boost game is displayed to the user via a graphical user interface on a mobile computing device. For example, the SCT boost game may be displayed on the electronic user device 1702. At block 2406, the neurostimulation device 2202 is activated to provide transcranial stimulation to the user while the user plays the SCT boost game. In some implementations, the electronic user device 1702 prompts to the user to activate the neurostimulation device 2202 with a set of operating parameters. In other implementations, control signals are sent to the controller 2216 to activate the neurostimulation device 2202.

Figure 25:
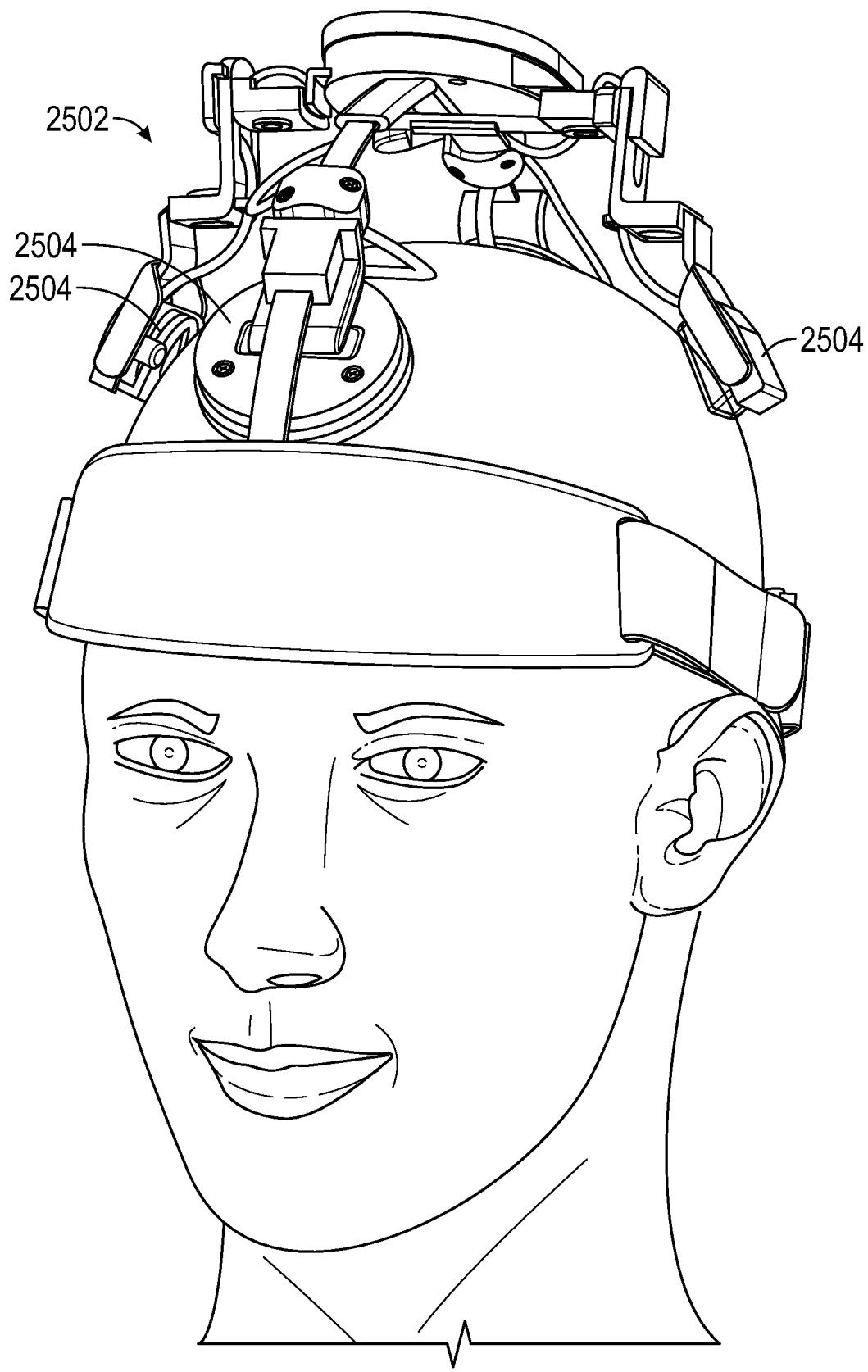
FIG. 25 is a diagram of an example of a neurostimulation device with optical stimulation, in accordance with some implementations of the present disclosure.

In some implementations, optical stimulation may be applied in additional to (or in place of) DC stimulation. Optical stimulation (for example, photobiomodulation (PBM) also known as low-level laser therapy or low-level light therapy (LLLT)) is a form of light therapy that utilizes non-ionizing forms of light sources. LLLT typically penetrates the scalp, skull, and brain parenchyma to at least a 1 centimeter depth. FIG. 25 is a diagram an example of a neurostimulation device 2502 with a plurality of optical sources 2504. The neurostimulation device 2502 applies optical stimulation through the plurality of optical sources 2504. The plurality of optical sources 2504 may emit light in the visible and near infrared spectrum. For example, LLLT may include optical stimulation at wavelengths in about the 650 nanometer to 690 nanometer range, about the 800 nanometer to 1,110 nanometer range, or a combination thereof. The plurality of optical sources 2504 may include, for example, light-emitting diodes (LEDs), low-power lasers, or both. The plurality of optical sources 2504 may be locating in a single array or in a cluster grouping. Operating parameters of optical stimulation may vary by specific wavelength range(s), duration of stimulation (for example, between about 10 minutes and 60 minutes) per session, and total power density delivered (for example, a minimum of 5 $mW/cm^2$, or up to 20 $mW/cm^2$). In some implementations, an oral antioxidant supplement is used in addition to LLLT in the management of, among other things, addiction and TBI.

Consistent with the above disclosure, the examples of systems and methods enumerated in the following clauses are specifically contemplated and are intended as a non-limiting set of examples.

Clause 1. A method for managing self-control impairment, the method comprising:
  placing a neurostimulation device on a head of a user;
  displaying, to the user via a graphical user interface of a mobile computing device, a self-control training (SCT) boost game; and
  activating the neurostimulation device to provide a transcranial stimulation to the user while the user plays the SCT boost game.

Clause 2. The method of any clause herein, wherein the SCT boost game is a first SCT boost game, wherein the method further comprising adjusting one or more operating parameters of the transcranial stimulation based on a performance of the user during a second SCT boost game that is played before the first SCT boost game.

Clause 3. The method of any clause herein, wherein the first SCT boost game and the second SCT boost game both target at least one similar cognitive process.

Clause 4. The method of any clause herein, wherein the one or more operating parameters of the transcranial stimulation include at least one selected from the group consisting of frequency, intensity, and duration.

Clause 5. The method of any clause herein, wherein the SCT boost game is a first SCT boost game, wherein the transcranial stimulation is a first transcranial stimulation, and wherein the method further comprises:
   activating the neurostimulation device to provide a second transcranial stimulation to the user after the user plays the first SCT boost game; and
   displaying, to the user via the graphical user interface, a second SCT boost game after a predetermined period of time following activation of the second transcranial stimulation.

Clause 6. The method of any clause herein, wherein the transcranial stimulation includes a direct current stimulation through a plurality of electrodes of the neurostimulation device.

Clause 7. The method of any clause herein, wherein the transcranial stimulation includes an optical stimulation with a plurality of optical sources of the neurostimulation device.

Clause 8. The method of any clause herein, wherein the SCT boost game is configured to target one or more cognitive processes selected from the group consisting of working memory, procedural memory, ecological assessment, cognitive flexibility, choice-making, time perception, timing accuracy, inhibitory control, and delay tolerance.

Clause 9. The method of any clause herein, further comprising:
   generating, by an artificial intelligence engine using one or more machine learning models, a profile of the user based at least in part on a performance of the user during the SCT boost game; and
   adjusting one or more operating parameters of the transcranial stimulation based on the profile of the user.

Clause 10. The method of any clause herein, further comprising generating, by the artificial intelligence engine, at least one of the one of more machine learning models based on boost game performance data of a plurality of users or data from check-in sessions of the plurality of users.

Clause 11. A system for managing self-control impairment, the system comprising:
   a neurostimulation device configured to be worn on a head of a user;
   a graphical user interface;
   one or more memory devices for storing instructions; and
   one or more processing devices configured to execute the instructions to:
      display, to the user via the graphical user interface, a self-control training (SCT) boost game, and
      activate the neurostimulation device to provide a transcranial stimulation to the user while the user plays the SCT boost game.

Clause 12. The system of any clause herein, wherein the SCT boost game is a first SCT boost game, and wherein the one or more processing devices are further configured to execute the instructions to adjust one or more operating parameters of the transcranial stimulation based on a performance of the user during a second SCT boost game that is played before the first SCT boost game.

Clause 13. The system of any clause herein, wherein the first SCT boost game and the second SCT boost game both target at least one similar cognitive process.

Clause 14. The system of any clause herein, wherein the one or more operating parameters of the transcranial stimulation include at least one selected from the group consisting of frequency, intensity, and duration.

Clause 15. The system of any clause herein, wherein the SCT boost game is a first SCT boost game, wherein the transcranial stimulation is a first transcranial stimulation, and wherein the one or more processing devices are further configured to execute the instructions to:
   activate the neurostimulation device to provide a second transcranial stimulation to the user after the user plays the first SCT boost game, and
   display, to the user via the graphical user interface, a second SCT boost game after a predetermined period of time following activation of the second transcranial stimulation.

Clause 16. The system of any clause herein, wherein the neurostimulation device includes a plurality of electrodes, and wherein the transcranial stimulation includes a direct current stimulation applied by the plurality of electrodes.

Clause 17. The system of any clause herein, wherein the neurostimulation device includes a plurality of optical sources, and wherein the transcranial stimulation includes an optical stimulation applied by the plurality of optical sources.

Clause 18. The system of any clause herein, wherein the SCT boost game is configured to target one or more cognitive processes selected from the group consisting of working memory, procedural memory, ecological assessment, cognitive flexibility, choice-making, time perception, timing accuracy, inhibitory control, and delay tolerance.

Clause 19. The system of any clause herein, wherein the neurostimulation device includes one or more sensors configured to capture sensor data indicating movement of the user, and wherein the one or more processing devices are further configured to execute the instructions to:
   detect, based on the sensor data, when the user has entered sleep, and
   generate an alert responsive to detecting that the user has entered sleep.

Clause 20. The system of any clause herein, wherein the neurostimulation device includes one or more sensors configured to capture sensor data indicating a scalp surface temperature of the user, and wherein the one or more processing devices are further configured to execute the instructions to:
   detect, based on the sensor data, when the scalp surface temperature of the user is greater than a threshold, and
   generate an alert responsive to detecting that the scalp surface temperature of the user is greater than the threshold.

No part of the description in this application should be read as implying that any particular element, step, or function is an essential element that must be included in the claim scope. The scope of patented subject matter is defined only by the claims. Moreover, none of the claims is intended to invoke 25 U.S.C. § 104(f) unless the exact words "means for" are followed by a participle.

The foregoing description, for purposes of explanation, use specific nomenclature to provide a thorough understanding of the described embodiments. However, it should be apparent to one skilled in the art that the specific details are not required to practice the described embodiments. Thus, the foregoing descriptions of specific embodiments are presented for purposes of illustration and description. They are not intended to be exhaustive or to limit the described embodiments to the precise forms disclosed. It should be apparent to one of ordinary skill in the art that many modifications and variations are possible in view of the above teachings.

The above discussion is meant to be illustrative of the principles and various embodiments of the present disclosure. Once the above disclosure is fully appreciated, numerous variations and modifications will become apparent to those skilled in the art. It is intended that the following claims be interpreted to embrace all such variations and modifications.

What is claimed is:

1. A method for managing self-control impairment, the method comprising:
   placing a neurostimulation device on a head of a user;
   selecting a self-control training (SCT) boost game configured to target one or more cognitive processes selected from the group consisting of time perception, timing accuracy, inhibitory control, and delay tolerance;
   determining a time duration for a transcranial stimulation;
   activating the neurostimulation device to provide the transcranial stimulation to the user for at least the time duration; and
   displaying, to the user via a graphical user interface of a mobile computing device, the SCT boost game while the neurostimulation device provides the transcranial stimulation to the user.

2. The method of claim 1, wherein the SCT boost game is a first SCT boost game, wherein the method further comprising:
   prior to selecting the first SCT boost game
      displaying, to the user via the graphical user interface, a second SCT boost game, and
      determining a performance of the user for the second SCT boost game, and
   subsequent to selecting the first SCT boost game
      setting one or more operating parameters of the transcranial stimulation based on the performance of the user for the second SCT boost game.

3. The method of claim 2, wherein the first SCT boost game and the second SCT boost game both target at least one similar cognitive process.

4. The method of claim 2, wherein the one or more operating parameters of the transcranial stimulation include at least one selected from the group consisting of frequency, intensity, and the time duration.

5. The method of claim 1, wherein the SCT boost game is a first SCT boost game, wherein the transcranial stimulation is a first transcranial stimulation, and wherein the method further comprises:
   activating the neurostimulation device to provide a second transcranial stimulation to the user after the user plays the first SCT boost game; and
   displaying, to the user via the graphical user interface, a second SCT boost game after a predetermined period of time following activation of the second transcranial stimulation.

6. The method of claim 1, wherein the transcranial stimulation includes a direct current stimulation through a plurality of electrodes of the neurostimulation device.

7. The method of claim 1, wherein the transcranial stimulation includes an optical stimulation with a plurality of optical sources of the neurostimulation device.

8. The method of claim 1, wherein the SCT boost game is further configured to target the one or more cognitive processes selected from the group consisting of working memory, procedural memory, ecological assessment, cognitive flexibility, and choice-making.

9. The method of claim 1, further comprising starting display of the SCT boost game to the user a predetermined period of time following activation of the neurostimulation device to provide the transcranial stimulation to the user.

10. A system for managing self-control impairment, the system comprising:
    a neurostimulation device configured to be worn on a head of a user;
    a graphical user interface;
    one or more memory devices for storing instructions; and
    one or more processing devices configured to execute the instructions to:
       select a self-control training (SCT) boost game configured to target one or more cognitive processes selected from the group consisting of time perception, timing accuracy, inhibitory control, and delay tolerance,
       determine a time duration for a transcranial stimulation,
       activate the neurostimulation device to provide the transcranial stimulation to the user for at least the time duration, and
       display, to the user via the graphical user interface, the SCT boost game while the neurostimulation device provides the transcranial stimulation to the user.

11. The system of claim 10, wherein the SCT boost game is a first SCT boost game, and wherein the one or more processing devices are further configured to execute the instructions to:
    prior to selection of the first SCT boost game
       display, to the user via the graphical user interface, a second SCT boost game, and
       determine a performance of the user for the second SCT boost game, and
    subsequent to the selection of the first SCT boost game
       set one or more operating parameters of the transcranial stimulation based on the performance of the user for the second SCT boost game.

12. The system of claim 11, wherein the first SCT boost game and the second SCT boost game both target at least one similar cognitive process.

13. The system of claim 11, wherein the one or more operating parameters of the transcranial stimulation include at least one selected from the group consisting of frequency, intensity, and the time duration.

14. The system of claim 10, wherein the SCT boost game is a first SCT boost game, wherein the transcranial stimulation is a first transcranial stimulation, and wherein the one or more processing devices are further configured to execute the instructions to:
    activate the neurostimulation device to provide a second transcranial stimulation to the user after the user plays the first SCT boost game, and
    display, to the user via the graphical user interface, a second SCT boost game after a predetermined period of time following activation of the second transcranial stimulation.

15. The system of claim 10, wherein the neurostimulation device includes a plurality of electrodes, and wherein the transcranial stimulation includes a direct current stimulation applied by the plurality of electrodes.

16. The system of claim 10, wherein the neurostimulation device includes a plurality of optical sources, and wherein the transcranial stimulation includes an optical stimulation applied by the plurality of optical sources.

17. The system of claim 10, wherein the SCT boost game is further configured to target the one or more cognitive processes selected from the group consisting of working memory, procedural memory, ecological assessment, cognitive flexibility, and choice-making.

18. The system of claim 10, wherein the neurostimulation device includes one or more sensors configured to capture sensor data indicating movement of the user, and wherein the one or more processing devices are further configured to execute the instructions to:
   detect, based on the sensor data, when the user has entered sleep, and
   generate an alert responsive to detecting that the user has entered sleep.

19. The system of claim 10, wherein the neurostimulation device includes one or more sensors configured to capture sensor data indicating a scalp surface temperature of the user, and wherein the one or more processing devices are further configured to execute the instructions to:
   detect, based on the sensor data, when the scalp surface temperature of the user is greater than a threshold, and
   generate an alert responsive to detecting that the scalp surface temperature of the user is greater than the threshold.

20. The system of claim 10, wherein the one or more processing devices are further configured to start displaying the SCT boost game to the user a predetermined period of time following activation of the neurostimulation device to provide the transcranial stimulation to the user.

\* \* \* \* \*